United States Patent
De

(10) Patent No.: US 10,845,363 B2
(45) Date of Patent: *Nov. 24, 2020

(54) CELL-SPECIFIC SIGNALING BIOMARKER ANALYSIS BY HIGH PARAMETER CYTOMETRY; SAMPLE PROCESSING, ASSAY SET-UP, METHOD, ANALYSIS

(71) Applicant: DeePath Medical Diagnostics, Inc., Costa Mesa, CA (US)

(72) Inventor: Jita De, Costa Mesa, CA (US)

(73) Assignee: DeePath Medical Diagnostics, Inc., Costa Mesa, CA (US)

( * ) Notice: Subject to any disclaimer, the term of this patent is extended or adjusted under 35 U.S.C. 154(b) by 129 days.

This patent is subject to a terminal disclaimer.

(21) Appl. No.: 15/969,566

(22) Filed: May 2, 2018

(65) Prior Publication Data

US 2018/0252708 A1 Sep. 6, 2018

Related U.S. Application Data

(60) Continuation-in-part of application No. 15/864,144, filed on Jan. 8, 2018, now Pat. No. 10,139,398, which is a division of application No. 14/647,414, filed as application No. PCT/US2013/072367 on Nov. 27, 2013, now Pat. No. 9,885,708.

(60) Provisional application No. 61/797,002, filed on Nov. 27, 2012, provisional application No. 61/797,006, filed on Nov. 27, 2012, provisional application No. 61/797,024, filed on Nov. 27, 2012, provisional application No. 62/500,072, filed on May 2, 2017.

(51) Int. Cl.
| | |
|---|---|
| *G01N 33/53* | (2006.01) |
| *G01N 33/543* | (2006.01) |
| *G01N 33/50* | (2006.01) |
| *G01N 15/10* | (2006.01) |

(52) U.S. Cl.
CPC ......... *G01N 33/5306* (2013.01); *G01N 15/10* (2013.01); *G01N 33/5005* (2013.01); *G01N 33/5091* (2013.01); *G01N 33/54366* (2013.01); *G01N 2015/1006* (2013.01); *G01N 2800/52* (2013.01)

(58) Field of Classification Search
None
See application file for complete search history.

(56) References Cited

U.S. PATENT DOCUMENTS

| | | | | |
|---|---|---|---|---|
| 7,248,360 B2 * | 7/2007 | Horchner | ............... | G01J 3/2803 250/458.1 |
| 2003/0176409 A1 * | 9/2003 | Offner | .................. | A61K 38/191 514/182 |
| 2014/0031308 A1 * | 1/2014 | Diane | ................ | G01N 33/5005 514/43 |
| 2018/0325947 A1 * | 11/2018 | Malik | .................... | A61K 35/28 |

OTHER PUBLICATIONS

Ornatsky et al. J. Immunological Methods 2010 361: 1-20 (Year: 2010).*

* cited by examiner

*Primary Examiner* — Changhwa J Cheu
(74) *Attorney, Agent, or Firm* — Convergence Intellectual Property Law P.C.; Jonathan Garfinkel

(57) ABSTRACT

The present invention recognizes that current clinical laboratory testing methods for multiparametric single cell analysis are limited to analysis of intact live cells, and are insufficient for identification of signaling activation profile defining certain cell types, including but not limited to neoplastic and immunologically activated cell subsets. One aspect of the present invention generally relates to marker selection in panels to include proteins routinely assessed in standard FCM, while preferably also incorporating markers for surface receptor proteins within activated signaling cascades. A further aspect of the present invention generally relates to panel design for the following indications in neoplastic and non-neoplastic clinical applications as examples of the technology: (a) identification of CML progenitor cell subsets in the setting of disease recurrence after treatment discontinuation or relapse due to treatment resistance, and (b) characterization of activated basophils to predict the severity of an allergic response. Another aspect of the present invention generally relates to methods to measure levels of surface and IC biomarkers in separate or combined assays for robust characterization of each or select cell compartment, and data analysis based on results from each or all method(s) used for optimal detection of the markers. A further aspect of the present invention generally relates to the identification and profiling of cell subpopulations based on analysis of surface markers including those associated with lineage and maturation of cell types and receptor proteins, and the corresponding IC phosphoproteins including those in activated signaling cascades to predict certain disease states or response to treatment.

11 Claims, 19 Drawing Sheets

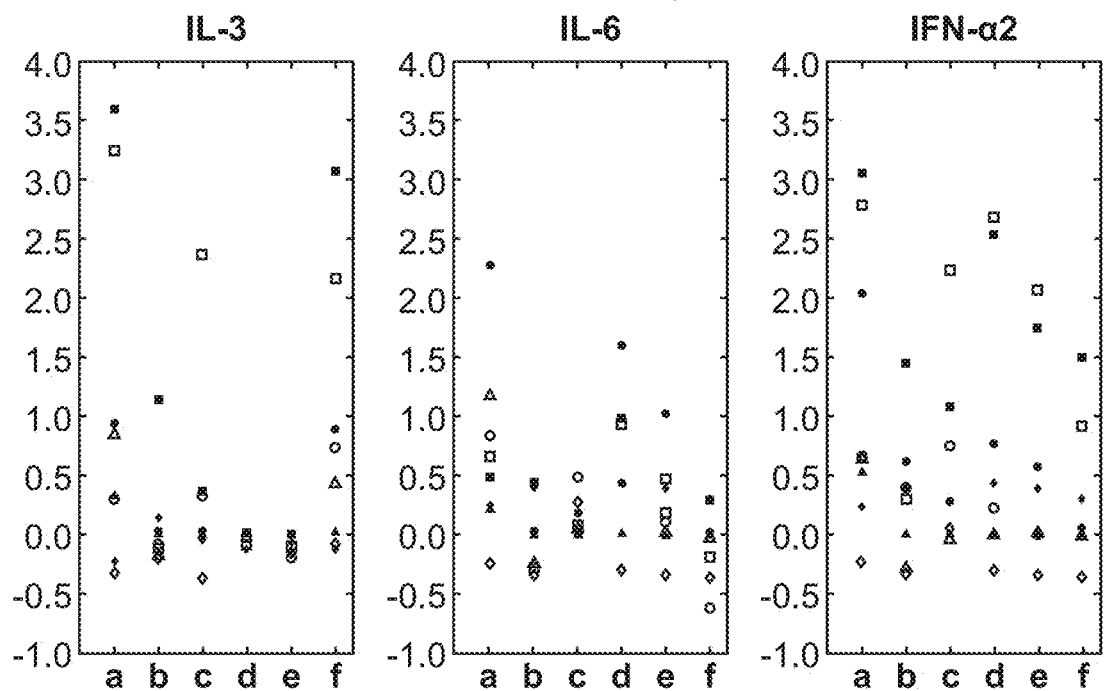
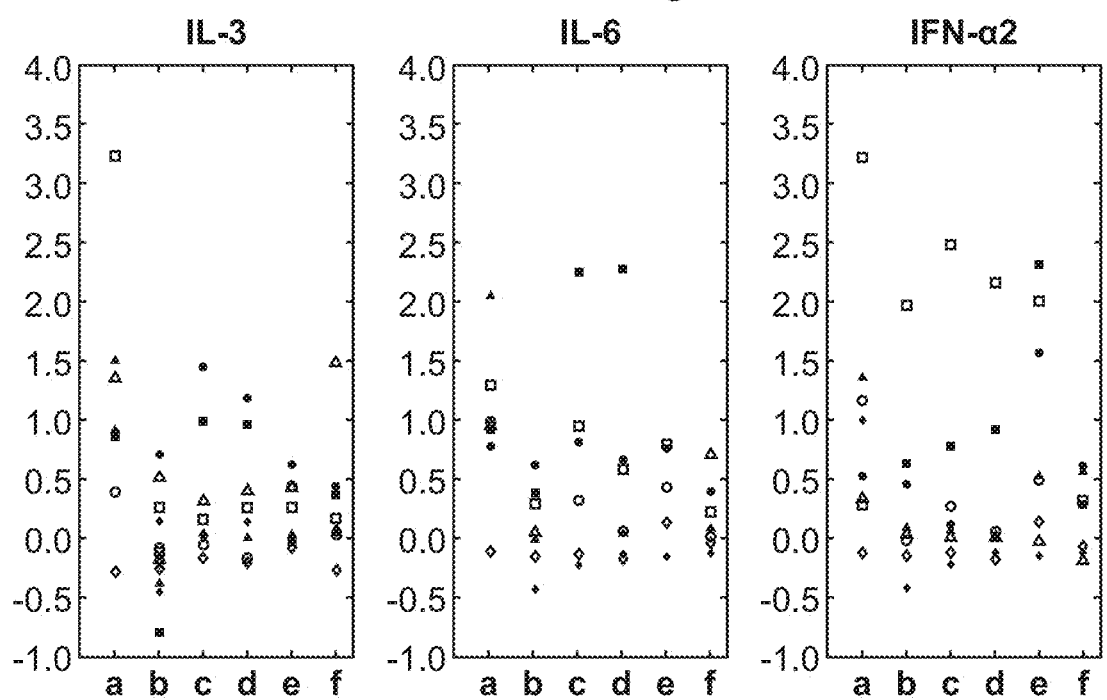
FIG. 1

Assay 1
Surface staining only
(*no fixation*)

| Detector | Marker | Detector | Marker |
|---|---|---|---|
| FL1 | Surface a | FL1 | Surface a |
| FL2 | Surface b | FL2 | Surface l |
| FL3 | Surface c | FL3 | Surface g |
| FL4 | Surface d | FL4 | Surface k |
| FL5 | Surface e | FL5 | Surface m |
| FL6 | Surface f | FL6 | Surface n |
| FL7 | Surface g | FL7 | Surface c |
| FL8 | Surface h | FL8 | Surface o |
| FL9 | Surface i | FL9 | Surface e |
| FL10 | Surface j | FL10 | Surface b |

Assay 2
a. Fixation → Surface staining → Permeabilization → intracellular staining b. Surface staining → Fixation and Permeabilization → intracellular staining

| Detector | Marker |
|---|---|
| FL1 | IC marker i1 |
| FL2 | Surface a |
| FL3 | Surface b |
| FL4 | |
| FL5 | Surface c |
| FL6 | IC marker i2 |
| FL7 | Surface d |
| FL8 | |
| FL9 | Surface e |
| FL10 | IC marker i3 |

FIG. 14

| Markers in 3-tube SCALPEL assay for CML | | | |
|---|---|---|---|
| Detector | Tube 1 | Tube 2 | Tube 3 |
| | | | |
| FL1 | CD45 | CD33 | p-CRKL (pY207) |
| FL2 | CD7 | CD10 | CD34 |
| FL3 | CD4 | CD3 | CD3 |
| FL4 | | CD45 | CD45 |
| FL5 | | | |
| FL6 | CD45RA | CD38 | p-p38 MAPK (pT180/pY182) |
| FL7 | CD19 | CD19 | CD19 |
| FL8 | CD8 | HLA-DR | |
| FL9 | CD56 | CD117 | p-STAT5 (pY694) |
| FL10 | CD127 | CD123 | |
| FL11 | CD3 | CD16 | CD11c |
| FL12 | CD14 | CD71 | CD127 |

| Tube4 |
|---|
| |
| CD45 |
| |
| CD13 |
| |
| CD127 |
| |
| |
| CD19 |
| CD20 |
| |
| CD117 |
| FVS 510 |
| CD16 |
| |

FIG. 15

| Markers in 2-tube SCALPEL Assay for Allergy Testing |||
|---|---|---|
| Fluorochrome | Tube 1 | Tube 2 (IC markers) |
| FL1 | CD45 | HLA-DR |
| FL2 | HLA-DR | p-ERK (pT202/pY204) |
| FL3 | CD3 | CD3 |
| FL4 | CD14 | CD45 |
| FL5 | CD63 | |
| FL6 | CD38 | p-p38 MAPK (pT180/pY182) |
| FL7 | CD19 | |
| FL8 | | |
| FL9 | | |
| FL10 | CD123 | CD123 |
| FL11 | CD16 | |
| FL12 | CD61 | CD61 |

FIG. 17

CELL-SPECIFIC SIGNALING BIOMARKER ANALYSIS BY HIGH PARAMETER CYTOMETRY; SAMPLE PROCESSING, ASSAY SET-UP, METHOD, ANALYSIS

CROSS-REFERENCE TO RELATED APPLICATIONS

This application is a continuation-in-part of application of U.S. application Ser. No. 15/864,144 filed on Jan. 8, 2018, which is a divisional application of U.S. application Ser. No. 14/647,414, which is a national stage entry under 35 U.S.C. 371 of PCT International Application PCT/US13/72367 filed on 27 Nov. 2013, which claims priority to U.S. Provisional Application No. 61/797,002, filed on Nov. 27, 2012, 61/797,006, filed on Nov. 27, 2012, and 61/797,024, filed on Nov. 27, 2012, and also claims benefit of priority to Provisional Application No. 62/500,072 filed on May 2, 2017, all of which are incorporated herein by reference in their entireties.

FIELD OF THE INVENTION

The present disclosure relates to methods for sample preparation and quantitation of antigenic biomarkers on individual cells in a multiparametric cell analysis platform such as mass cytometry and also the fields of cell biology, signal transduction, oncogenic signaling pathways, flow cytometry, and single cell analysis.

BACKGROUND

Comparison of primary neoplastic or immunologically activated cells with control cells of same lineage has not been undertaken to show signaling nodes that are of particular significance due to high signaling activity in individual cell-types of myeloid neoplasms. Dynamic signaling states can be compromised when samples are cryopreserved. Thus, phospho-flow analysis performed on fresh samples can be theoretically more informative in identifying previously unidentified signaling aberrations than analysis performed on preserved samples.

Phospho-flow assays, which have typically been performed by fluorescent flow cytometry (FCM), have limitations due to the number of colors available per analysis tube. At best, fluorescent cytometry allows 18-20 markers to be evaluated simultaneously. However, overlap of fluorescence emission spectra requires set up of compensation settings that can often be time consuming. Further, tandem dyes can break down and emit signal at a different wavelength than expected, confounding results. Most commercial instruments are capable of analyzing less than 12 antibodies/tube. Thus, evaluating both lineage markers expression on the cell surface and functional intracellular (IC) markers in a single tube assay has not been feasible. Multi-tube analysis can be time consuming and has precluded precise mapping of functional activity to cell-type, in particular rare cell-types (such as leukemic stem and progenitor cells, dendritic cells, clonal T cells, etc.), some of which require at least 8-9 lineage- and maturation-associated surface markers (such as but not limited to CD3, CD4, CD8, CD11c, CD14, CD16, CD19, CD33, CD34, CD45, CD45RO, CD56, CD90, CD117, CD123) for accurate cell type delineation based on expression level, and presence or absence of markers. Fluorescent-labeled antibodies are generally more expensive and less stable than metal-tagged antibodies.

New methods are needed for analysis of large numbers of cell surface and IC markers simultaneously.

Multiparameter FCM facilitates analysis of multiple antigenic markers concurrently on individual cells in heterogeneous cellular mixtures such as that in blood, bone marrow, lymph node, and needle aspirates (1). In clinical diagnostics, this technology is used to identify immune cells in tissues of the hematopoietic system, including blood, bone marrow, and lymph nodes. Cell types in the blood routinely identified by this method include T cell subsets, B cells with kappa or lambda expression, monocytes, natural killer (NK) cells, eosinophils, basophils, and neutrophils. Common leukocyte antigen or CD45, and light scatter (forward and side angle) features are universally applied to distinguish between lymphocytes, monocytes, and granulocytes. Other surface protein antigen markers are included in panels for cell lineage identification and broadly their function, such as CD4 helper and CD8 suppressor T cells. In addition to the above cell types identified in the blood, healthy cell types in healthy bone marrow typically resolved by a standard set of 20-30 markers tested in multiple tubes by FCM are the following: CD34+ physiologic blasts, hematogones, plasma cells, and maturing myeloid precursors. Due to the limited availability of commercially available fluorochrome-conjugated antibodies of desired specificity and detectors or channels on clinical flow cytometers, the number of antigen dimensions simultaneously assessed is generally 10 or less. Hence, to identify and characterize the features of all expected normal cells and ascertain abnormalities, multiple, usually 5 to 6, panels of surface markers are designed for the specimen tested in multiple tubes. Intensity of expression (positive, negative, dim, moderate, bright) of a series of differentiating markers are thus evaluated on each cell and cells similar in antigen expression profile are grouped through hierarchical gating or high dimensional clustering algorithms.

The multiplexed capabilities of FCM that allow distinction of abnormal cell populations with aberrant antigen expression profile and determination of the percentage of such populations in addition to the overall cell composition, make it a robust high throughput analysis tool for diagnosis of hematologic neoplasms. The following are examples of abnormalities detected by FCM tests for clinical applications (2):

1. Monoclonal B cells and plasma cells with abnormal cytoplasmic kappa/lambda ratio.
2. Neoplastic or reactive conditions with abnormal ratio of CD4 and CD8 T cell subsets, aberrant T cells, loss of normal T cell associated antigens.
3. Abnormal myeloid maturation pattern, as a possible indicator of myelodysplasia.
4. High grade myelodysplasia, with increased CD34+ myeloid blasts.
5. Basophil activation in allergy using CD63 expression as a marker of response to an allergen.
6. Abnormal increase of NK cells and receptor polymorphism.
7. Acute myeloid leukemia with increased CD34+/− myeloid blasts and/or promonocytes, and/or monoblasts.
8. Precursor B lymphoblastic leukemia, with increased CD34+B lymphoblasts.
9. Precursor T lymphoblastic leukemia with CD34− and/or terminal deoxynucleotidyl transferase (tdt)-expressing T lymphoblasts.
10. Abnormal expansion of rare cell types such as progenitor cells, dendritic cells, mast cells, and certain subsets of B, T, or NK cells associated with a disease condition.

11. Neoplastic conditions and reactive conditions such as autoimmune or other conditions with a mixture of immune cell infiltrates.

Despite the wide clinical applicability of FCM, functional attributes in abnormally activated signal transduction pathways or cellular processes are not a routine part of assessment for the purpose of discerning prognostically relevant cell types in clinical diagnostics. Thus, signaling activation as a feature that discerns cell subpopulations is not routinely analyzed. Instead, surface immunophenotype is relied upon for making such distinction. This presents a gap, being a long-felt and unmet need, in the field as surface markers alone are insufficient in distinguishing certain cell types such as but not limited to: a) leukemic stem and progenitor cells from physiologic blasts and hematogones, and b) activated basophil subset as an allergic response. Also, immunophenotypic criteria establishing a "neoplastic" v. reactive and immunologically activated cell subpopulation with prognostic relevance are not well understood. A classic example is chronic myeloid leukemia (CML), a stem cell neoplasm that manifests as an expansion of myeloid precursors with relatively normal maturation. Thus, maturation-associated surface markers in neutrophils, i.e. CD10, CD11b, CD13, CD16, CD33, CD66, KIT/CD117, IL3R/CD123, HLA-DR are not sufficient to distinguish a myeloid cell arising from a CML stem cell vs. a myeloid cell arising from a normal stem cell. Similarly, CD34+ CML blasts are indistinguishable from CD34+ physiologic myeloid blasts on the basis of surface phenotype. Multipotent CML progenitors are directed towards myeloid proliferation preferentially over lymphoid proliferation in part due to environmental cues controlled by BCR-ABL activity (3). Whereas, post-therapy, the distinction of residual CML progenitor cells may have diagnostic value, such is not possible with the current technology. Detection of these progenitor cells in routine diagnostics has been hampered by the lack of defining markers, and no known way to assess signaling molecules activated due to BCR-ABL kinase activity by current methodologies in diagnostic cytometry.

Similarly, in acute myeloid leukemia, post-therapy minimal residual disease can be challenging to identify for leukemia with minimal deviation in surface phenotype in the CD34+ myeloid blasts. Distinction from hematogones can likewise be a challenge for diagnosing minimal residual disease in acute lymphoblastic leukemia. Identifying rare neoplastic cell subpopulations based on an activated state as assessed by expression of phosphoproteins has been hampered for several reasons, such as but not limited to the following:

One, to detect IC phenotypes such as an activated state of certain kinases, the cells have to be subject to fixation in a biologically activated state and permeabilization for detection of certain IC epitopes (4). The cells are fixed after stimulating with cytokines or growth factors that induce the signaling pathways and can enhance their detection. For pharmacodynamics assays using phospho-flow methods, cells are fixed as such to capture the effects, i.e. fold-change above unstimulated, of drug or a growth factor-mediated signaling pathway. Formaldehyde-based fixatives crosslink proteins and hence are a desired fixative for analysis of IC phosphoproteins captured in an activated state. Cell fixatives contain alcohol or formaldehyde or paraformaldehyde, and permeabilization is performed by methanol reagents (5). These formalin and alcohol reagents are detrimental to most surface epitopes and cause cells to aggregate. Thus, these harsh treatments preclude accurate analysis of surface markers, which should ideally be performed on live cells, thus significantly limiting assessment of cell lineage- and maturation-associated proteins expressed on the cell surface of the same cells in the experiment.

Second, due to a limited number of filters and detectors on a fluorescence flow cytometer, a limited number of antigen dimensions can be assessed simultaneously on each cell. Although as many as 17 colors are theoretically possible in multiparameter cytometry (6), enabling the assessment of 19 parameters including scatter properties on each cell in one tube, there are substantial technical limitations to increasing the colors beyond 8-10. Recent development of brilliant violet fluorophore reporters have addressed some limitations in such assays due to their brightness thus improving sensitivity (7), and making them suitable for IC markers, yet a majority of the blockades to further development remain.

These include instrument factors such as costliness and bulkiness of additional laser and filter sets, limited available fluorophores and overlapping emission spectra, unstable compounds with tendency of breakdown causing spillover, and low intrinsic brightness precluding their use for low density antigens. These factors limit the true availability of dyes and channels, and in turn the types of cellular parameters assessed in clinical FCM. Thus, careful design of panels and selection of antibody conjugates with the appropriate instrumentation can become necessary, which can limit the flexibility and design of such panels.

These shortcomings have also limited the scope of phospho-flow experimentation to simpler systems such as cell lines and frozen mononuclear cells, resulting in yet to be unsolved barriers to advancing the technology. This unfortunate state of the art poses limitations on cell analysis in complex biologic samples with often >20 different unique identifiable cell types. Many small or rare cell subpopulations such as effector and memory T cell subsets, functional NK cells, dendritic cells, activated basophils, and leukemic stem and progenitor cells are not routinely assessed with a standard set of antibodies that only identify major cell types (i.e. neutrophils, monocytes, basophils, eosinophils, B cells, T cells, and NK cells). Additional tubes of antibodies and often more than the standard 8-10 color panels are necessary or desirable to accurately identify such rare cell types of clinical relevance. Deciphering the cellular heterogeneity, such that some, most, substantially all, or all abnormally expanded immune cell types, are distinguished from the other cells can be relevant for treatment decisions.

Massive multiplexing of antigens tested in high parameter cytometry can be achieved through the recent technological advance employing mass spectrometry-based detection system for potentially measuring up to 100 antibodies simultaneously on each cell (8). Mass cytometry enables resolution of increasing number of cell subpopulations, by precise measurements of n dimension(s), to decipher the cellular components in heterogeneous cell specimens. In part this has been possible by the selection of appropriate surface and IC marker combinations and modulators to capture activated functional states in experiments that are akin to the traditional phospho-flow experiments. Through assessment of signaling activation networks, gathering of empirical evidence for biologic phenomena such as severity of clinical symptoms, treatment response or resistance, and disease recurrence can pave the way for discovery of cell-based biomarkers for prediction. However, a robust approach to capturing such signaling biomarker data for translation into the clinical laboratory for clinical applications has been lacking.

While allowing for extensive profiling of individual cells, the disadvantages of the mass cytometry technology include the high instrument cost, substantial (as much as 70-90%) cell loss in sample processing, and lengthy data acquisition times, precluding its use as a clinical diagnostic test. Although a plethora of surface and IC markers including receptors and intracellular phosphorylated proteins can be assessed in the same tube, the requisite cell fixation to capture activated proteins for their measurement again obviates accurate assessment of surface markers in the same assay. Therefore, this presents a gap, being a long-felt and unmet need, in the technological capabilities for combining cell identification with multi-analyte functional profiling of biological pathways. In essence, measuring some or most substantive abnormalities in protein expression levels in order to characterize the dynamic range of such antigens including relevant modified forms that can define and characterize a multitude of non-overlapping cell types is not possible with the current technology. Thus, cell-based assays that generate cell-specific protein expression profiles and patterns defining particular disease states based on functional attributes are not available for diagnoses and prognostication.

The present invention addresses these shortcomings and roadblocks in the state of the art, and provides related and additional benefits as well.

BRIEF SUMMARY OF THE INVENTION

The present invention recognizes that current laboratory testing methods are limited to analysis of intact live cells, and are insufficient for identification of signaling activation profile that define certain cell types, including but not limited to neoplastic cell subsets. To detect all or substantially all cell types of significance or of interest in a specimen, analysis of functional attributes such as abnormal signaling activity is of high interest. The definition of cell clusters based on expression levels and activities of effector proteins of certain rare cell types can be achieved through concurrent assessment of a combination of surface markers and signaling markers, with a panel design of minimum set of markers across multiple tubes in a way that allows both detection and quantification of these cell types in the blood or other sample source.

Abnormal activation of survival pathways is a sina qua non in many disease states; representing a marker for abnormal cell detection. For instance, constitutive STAT5 activation is a common feature of myeloid blasts in myeloproliferative neoplasms. Activation of p38 MAPK activation is also found in leukemic cells, while also associated with reactive state such as basophil degranulation in allergy. Analysis of reliable phenotypes defining abnormal cell types can be performed by phospho-flow cytometry experiments to identify cells in particular pathologically activated states by measuring expression of a set, typically 1-4, of phosphoprotein(s). This allows abnormal cell identification not based on lineage markers on the cell surface as traditionally done, but using key effector protein biomarker(s) within a disease-associated cellular pathway. Certain activated phosphoproteins defining an aberrant phenotype can be considered stable attributes as they reliably identify cells with certain abnormal cell process. The presented examples demonstrate the inclusion of activated IC markers as a primary selection marker to identify abnormal cell types in their fixed state, and to further characterize those cells using other markers such as those that define the cell lineage through live cell analysis in separate tube(s).

A first aspect of the present invention includes selection of markers in antibody panels for multiplexed assessment of only the surface markers in one assay, and a combination of surface and IC markers in another assay. The surface markers, to include but are not limited to ones that identify and quantify cell types of interest, are essentially all tested on live cells or presumptively live cells. Thus, the first assay is preferably performed on non-fixed cells, more preferably live cells, while in the second assay, the cells are fixed for evaluation of IC markers best analyzed after fixation of particular activated states.

A second aspect of the present invention includes the selection of such markers in the above-mentioned panels for the specific purpose of identifying particular cell types of known immunophenotype and prognostic relevance in certain disease states such as leukemia. These cell types of relevance include but are not limited to expanded immune cell types, such as T regulatory cells, functional NK cells, memory B cells, and leukemic progenitor cell types. This aspect of the present invention relates to methods to accurately detect neoplastic or reactive cell subpopulations, providing the CML progenitor cell types as an example to differentiate lymphoid v. myeloid cell subsets with identical or similar IC features, and quantify their proportions relative to other cells in the blood.

A third aspect of the present invention relates to methods to treat cells in each of the two assays for desired and in some instances enhanced surface staining of unperturbed live cells and IC staining of fixed cells. The unaltered neoplastic cells can have inherently high neoplastic activity that can be captured by fixing the specimen in an unperturbed state, so as to detect the cells (in some instances only the cells) with oncogenic and/or constitutive signaling activities above the baseline regulated state of normal cells. This aspect of the present invention addresses methods that enhance detection of neoplastic cells.

A fourth aspect of the present invention relates to analysis of data for high dimensional identification and profiling of cell subpopulations defined by a certain activated biologic state measured in fixed state, and optionally characterized based on an extended set of surface markers assessed on cells such as but not limited to live cells. The approach to deriving a certain cell type, partly delineated by one approach (or assay) that requires interrogating IC features, and further characterized relative to other cells by another approach that is staining live cells, such that the individual data outputs are considered in the context of known cell types expected in the particular biologic state. In this way, though assay methodologies are distinct but performed on the same overall specimen, analyzing different features or characteristics of the same cell types by different methods that best preserve the integrity of the epitopes tested by each of the method, an extended profile of the surface and IC dimensions of particular cell types is derived. In this way, confirmation of the presence, absence, or quantity of relevant cell types is obtained, which can improve the accuracy of the detection, evaluation, and analysis of such cells.

In a further aspect, a unique sample preparation method is provided for phos-flow analysis that incorporates a pre-fixation cooling step that lowers baseline signaling activity and results in a higher fold-change or distance between the induced and baseline state. A staining step for cell identification is performed prior to fixation. The method applies to modified samples that require surface staining for cell identification for applications that require use of live cells for further single cell analysis.

The method applies to cell lines, frozen or fresh mononuclear cells, fresh human samples including blood, bone marrow, tissue biopsies and aspirates, and other sample for biomedical research and to test novel inhibitors by cell-based pharmacoproteomic assays.

In another aspect, a sample preparation method is provided that allows fixation of a sample in its fresh state for baseline activity assessment. Simultaneous assessment of baseline signaling activities and cell identification is performed in the same experiment and applied for diagnostic and prognostic assays. The sample can be any human sample or solid tissue for clinical diagnostics including blood, marrow, fine needle aspirates, and tissue biopsies comprised of a heterogeneous mixture of cells requiring cell-type identification. A strategy that combines a baseline evaluation by fresh sample fixation with surface staining performed post-fixation; and induced fold-change evaluation where surface staining is performed pre-fixation.

In another aspect, a novel combination of receptors and signaling markers is provided, including IL3R, IL7R, p-STAT5, p-STAT3, and p-p38 MAPK for identification of cells that have abnormally high signaling activities and based on their cell type can predict the cause of relapse, guide therapy, and prognosticate disease outcome. The sample can be any human sample or solid tissue including blood, marrow, fine needle aspirates, and tissue biopsies comprised of a heterogeneous mixture of cells requiring cell-type identification. This antibody panel applied in high throughput cytometry assays for prognostic and diagnostic evaluation and drug discovery in CML, and other acute and chronic myeloproliferative leukemias, and Ph+ acute lymphoblastic leukemia.

In another aspect, data analysis methods are provided based on user selection of variables such as cell-types, ex vivo perturbations or conditions, select IC analytes. High dimensional plots generated by select parameters can result in patterns that allow interpretation of multiparameter cytometry data and discover correlations such as between biochemical pathways associated with individual pathobiology. Cell type-specific proteomic profiles (mapping antigen expression profile to the identified cells) are provided which can facilitate data interpretation through intuitive visualization of post-gated data with simultaneous displays of cell types, and proportions, that indicate the form and quantity of disease burden. Quantitative data inclusive of cell fractions and expression levels of biomarkers enable comparison of datasets acquired from different time points to monitor therapy response. High dimensional plots based on selection of certain parameters that facilitate interpretation of high parameter datasets are provided.

BRIEF DESCRIPTION OF THE DRAWINGS

FIG. 1 illustrates cytokine-induced fold-change above baseline when using the pre-fixation staining method in chronic-phase CML patient compared to control for selected cell-types (a. monocytes, b. neutrophils, c. B cells, d. CD4 T cells, e. CD8 T cells, f. Basophils) and IC protein readouts (square: p-STAT5, circle: p-STAT3, triangle: p-p38 MAPK, and diamond: total IKB kinase). By this method, in myeloid lineage cells (neutrophils, monocytes, and basophils), all patient cells have higher IL3- and IFN☐2-induced p-STAT5 compared to normal counterparts. In monocytes and CD4 T cells, IL6-induced p-STAT3 compared to normal control cells. These fold-change are less delineated in post-fixation staining method, in part due to high baseline activities in the latter method.

FIG. 14 illustrates but one aspect of an assay set-up whereby the sample of live unperturbed cells in tubes 1 and 2 is stained with panels of antibodies towards surface antigens and the sample in tube 3 is stained with a set of surface markers (denoted by alphabets) and IC markers (denoted by alphabet and a number) post-fixation.

FIG. 15 depicts an illustration of but one aspect of panel design to specifically identify CML cells based on expression of p-CRKL marker, for identification of cells with activated BCR-ABL, and additional phosphorylated proteins, while characterizing their surface phenotype for expression of CD34, CD3, CD19 in the same tube, and additional surface markers measured on live cells in tubes 1 and 2. Tube 4 is a hypothetical design for minimal markers in an assay that could potentially identify 3 CML subpopulations in blood.

FIG. 16A shows individual differences in CD63 expression on basophils in control subjects—the effect of ex vivo treatment of the blood sample from healthy controls. Dotplots show variable percentage of basophils expressing CD63 and p38MAPK activation in response to anti-IgE. There is no effect to peanut (PN) treatment. FIG. 16B shows basophil response to peanut in an allergic subject—the effect of ex vivo treatment of a blood sample from a subject with peanut (PN) allergy. Dotplots show a subset of basophils expressing DC63 and p38MARPK activity in response to anti-IgE and PN. FIG. 16C shows patient-specific differences in CD63 expression on basophils—the individual differences in the effect of ex vivo treatment of blood samples from subject with peanut (PN) allergy. Dotplots show variability in CD63 response to peanut extract. Whereas upregulation of p38MAPK activity and CD61 expression are identified in a subset of basophils in both subjects, the expression of CD63 is detected in P3, but not P5.

FIG. 17 depicts an illustration of a panel designed to specifically detect the activated basophils while determining CD63 expression on that subset.

DETAILED DESCRIPTION

Figure 2:
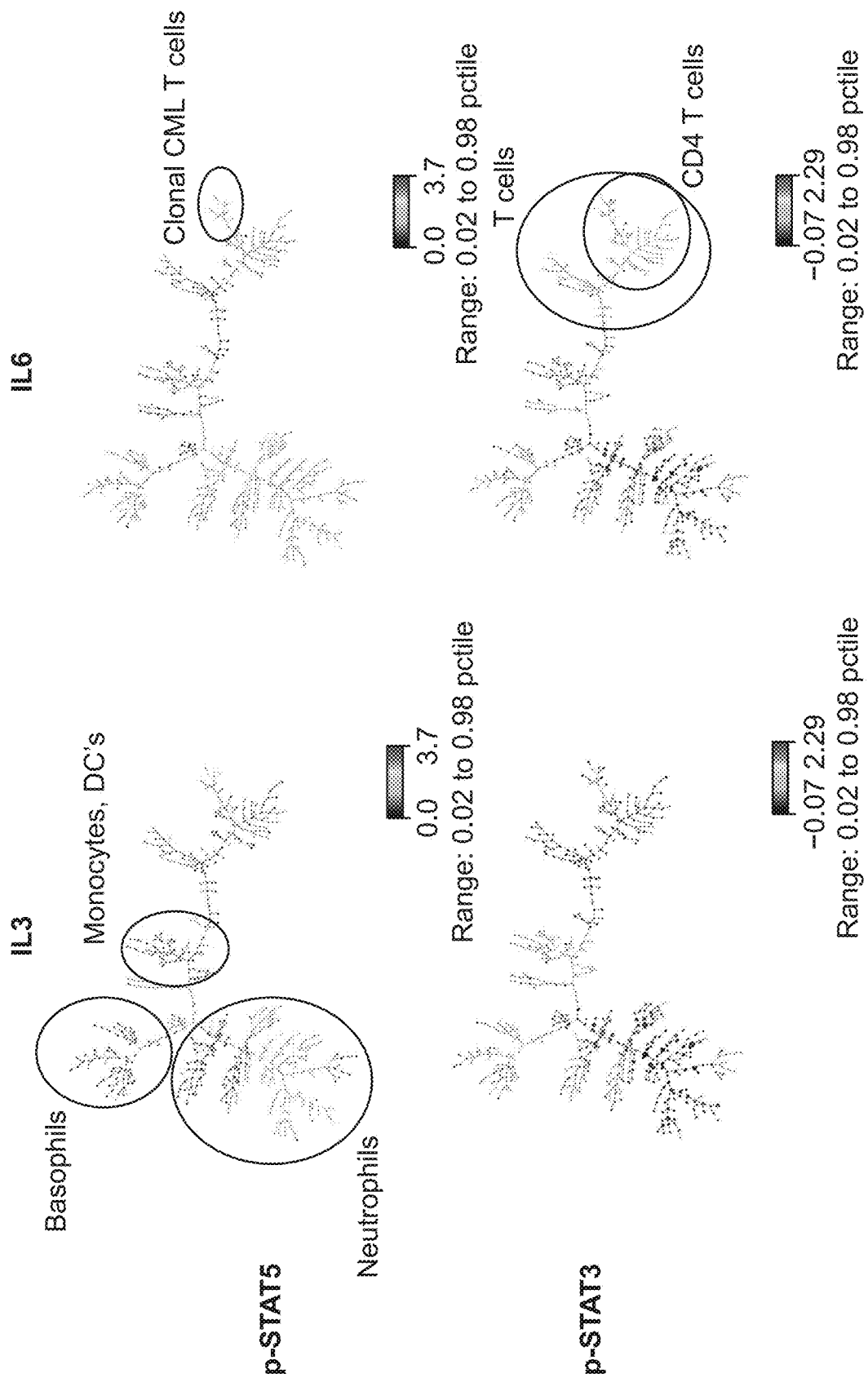
FIG. 2 depicts SPADE analysis performed for high dimensional clustering of cells to show differential induced STAT5 and STAT3 activities in the chronic phase CML blood sample. The analysis shows high induced IL3-STAT5 activity in cells arising from common myeloid progenitors (monocytes, myeloid DCs, neutrophils, basophils) and IL6-STAT3 activity in monocytes and CD4 T cells. Increased IL3-STAT3, STAT5 activity in CD33$^{hi}$ cells (basophils and monocytes) suggests correlation between STAT5 activity and CD33 expression. IL3, IL6-STAT5 activity is a possible marker of CML (BCR-ABL+) clonal T cells, while IL6-STAT3 activity is high in all CD4 T cells.

In hematopoietic stem cell neoplasms treated with therapies that selectively target the proliferative cell compartment, the level of residual relatively quiescent progenitor cell compartment can be of prognostic relevance. Identification of these progenitor cell subpopulations can be achieved through functional assessment of oncogenic signaling activities of pSTAT5 and pp38MAPK, as the standard surface markers cannot reliably distinguish neoplastic progenitors.

Variations in functional responses of pathologically activated cells can be predictive of certain clinical states. At present, the basophil activation test for allergic conditions is based on expression of CD63 on activated basophils, as a marker of pathologic degranulation. However, this is not a reliable marker as in some allergic subjects, possibly ones with the known "non-releaser" phenotype, there is lack of CD63 expression on basophils. Thus, pp38 MAPK is a more robust marker for activated basophils in peanut allergy subjects.

Having redundant or common markers in the panels enhanced for surface and IC marker evaluation allows cross correlation of the results. This approach surmounts the limitations of current state of the art fluorescence FCM (such as fluorophore overlap and breakdown of tandem conjugates resulting in spillover between detector channels) by limiting the analysis to 8-11 markers that can be reliably measured in each tube.

Since measuring phosphoprotein levels generally requires fixation using current methods, which can often compromise cell surface epitope binding, performing assays for assessing the surface and functional markers in separate tubes precludes fixation of the cell sample that is analyzed for majority of the surface markers. This approach allows determination of the basic composition of a cell mixture, such as peripheral blood, while performing extended profiling of select cell subpopulations through a robust set-up for surface and IC dimensions.

As a non-limiting introduction to the breadth of the present invention, the present invention includes several general and useful aspects, including:

1) Combination of antibodies in a panel to assess the routine cell surface proteins, while selectively including certain receptors within activated signaling cascades;
2) Panels of surface markers and IC markers for identification of CML progenitor cells;
3) Panels of surface and IC markers for identification of activated basophils as an allergic response;
4) Methods to measure levels of surface and IC markers in separate or combined assays for each or select cell compartment, to avail data for combined analysis including IC phosphoproteins for functional cell identification
5) Detailed characterization of cell subpopulations through data analysis by cross-correlation of the results derived by each method; thus generating a profile of cell types with high activities of signaling molecules associated with a certain disease state or response to treatment.

These aspects of the present invention, as well as others described herein, can be achieved by using the compositions, articles of manufacture, and methods described herein. To gain a full appreciation of the scope of the present invention, it will be further recognized that various aspects of the present invention can be combined to make desirable embodiments of the invention.

With the introduction of improved flow cytometers with additional lasers such as 405 nm violet and 532 nm green, this allows excitation of dyes in a wide range of wavelengths than previously possible with the 488 nm blue and 633 nm red lasers. The present invention includes the approach for measuring levels of expression of surface and IC antigen markers in at least two tubes such that the first assay in tube 1 (and 2, and additional tubes, for more markers) analyzes the surface markers (a, b, c, d, e, f, g, h, i, j, k . . . ) on cells, preferably non-fixed cells, more preferably live cells, while the second assay in tube 3 analyzes select surface markers along with IC markers of interest (a, b, c, d, e . . . a1, a2, a3, . . . ) in fixed cells. The first assay is designed to preferably identify the major and minor cell subpopulations for a comprehensive or more complete analysis of various non-overlapping or unique cell subpopulations by immunophenotypic analysis of ONLY the surface markers. In doing so, cellular subsets are characterized based on numerous surface parameters, including lineage and maturation markers in one or two tubes set up for staining of surface markers in a way that can be preferably performed on live cells without the use of harsh fixatives or cell permeabilization reagents. The second assay, designed to preferably identify cells with abnormal properties such as activated oncogenic signaling networks, is performed by treating the sample with reagents appropriate for functional analysis.

Cell subset identification can be based on a pattern of IC marker expression that can predict the signaling network profile, while a precise assessment of lineage and maturation can be attained through analysis of live cells. The purpose of each assay is to extract independent sets of data that together can allow characterization of both the surface and IC dimensions in various cell subpopulations. A small set of surface markers (typically including but not limited to 5 antibodies) is selected for lineage characterization in the second assay. These common markers allow for data to be compared across the two (or more) different assay set-ups, to ultimately derive the expression levels of all proteins to define cell subpopulations and quantitate the percentage of the individual subpopulations. Clusters in high dimensional space are characterized for proportions of individual cell types and expression level of redundant markers in the context of expectation based on prior knowledge of the neoplastic condition.

In isolation, neither assay alone is as desirable as the combination because the information generated through each has its own value, and the overall interpretation requires both levels of expression data. Additionally, because the two assays are set up differently, the data can preferably only be interpreted through robust high dimensional analysis taking into consideration technical variables that impact the data output from each one. For example, the intensity of the common surface markers can be diminished resulting in lower signal to noise ratio due to non-specific epitope binding when using methods aimed to enhance IC cytoplasmic or nuclear staining of functional markers. These factors can in part be mitigated by selection of antibodies to antigens more resilient to fixatives and performing robust extrapolations based on expected profile of known cell types.

In the scenario of CML, multipotent progenitors arising from the CML stem cell, though primitive (lacking in substantial lineage commitment), have a certain level of directionality that can allow distinction between progenitor cell types. This distinction is relevant since T cells in general lack oncogenic potential, unlike the oncogenic B cells and myeloid cells. In general, the use of FCM in CML is limited to deriving the proportion of CD34+ leukemic blasts when normal precursors are reduced, such as in chronic phase or accelerated and blast phase CML. Given the lineage plasticity inherent in stem and progenitor cells, their identification and monitoring post therapy are likely of clinical significance. Also, the cellular source (T cells v. B cells v. myeloid cells) of the BCR-ABLI transcript could be a predictor of risk of relapse. Finally, the relative proportions of the progenitor cell types can be of prognostic relevance in stratifying patients who would sustain long-term treatment-free remission (based on successful elimination of cells with oncogenic potential, thus achieving a deep remission).

Figure 16A:
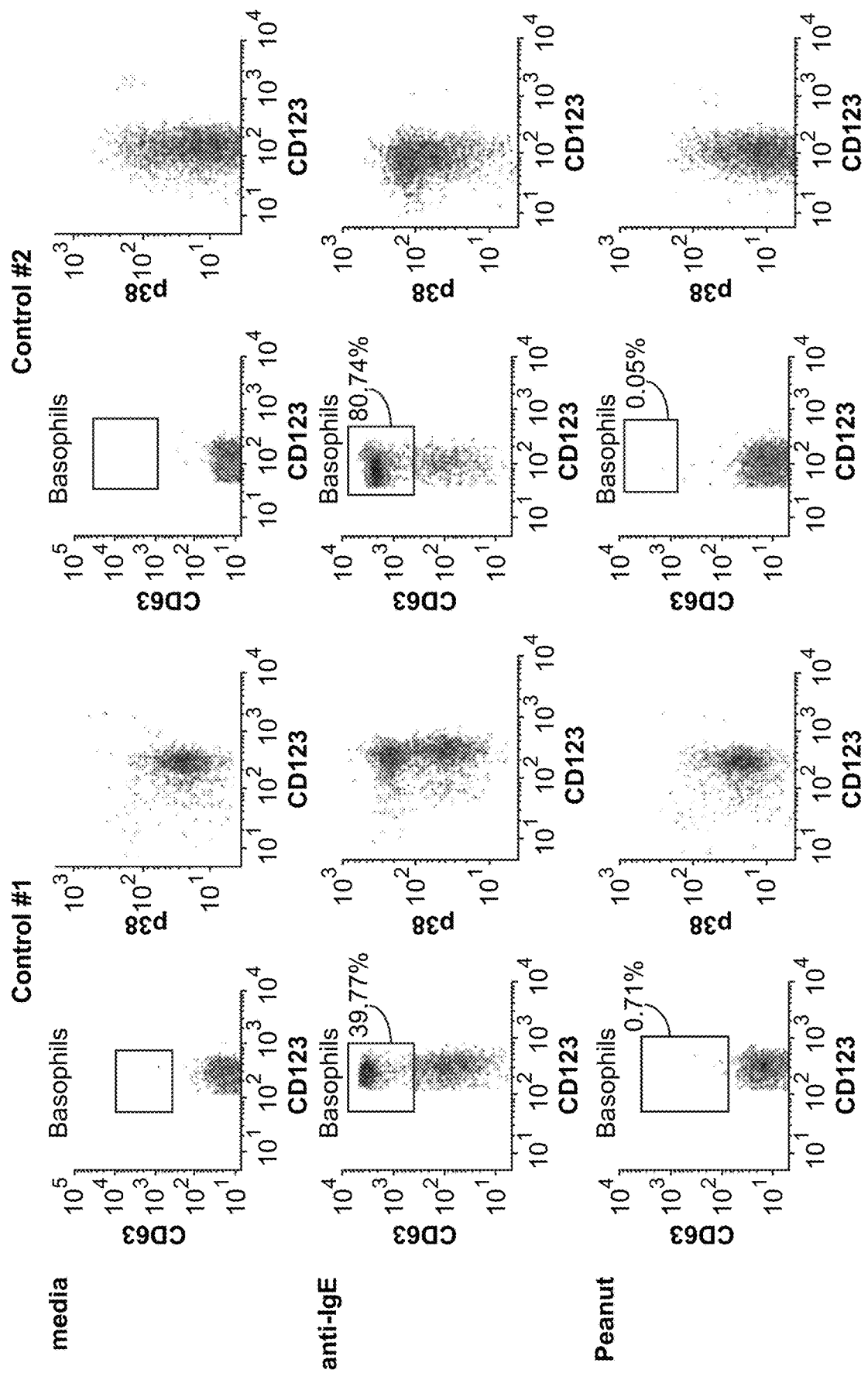
FIG. 16A.
Figure 16B:
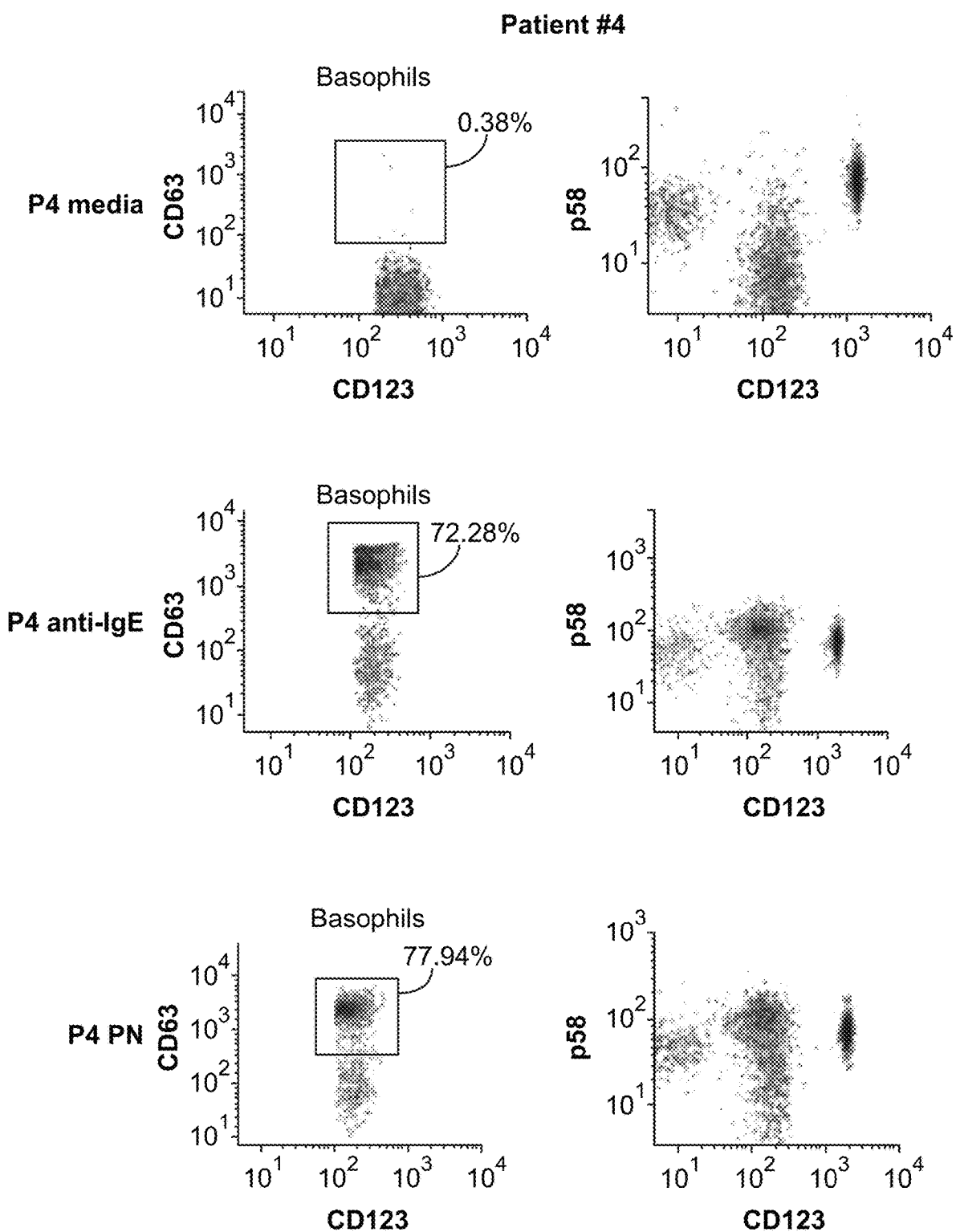
FIG. 16B and FIG. 16C show the analysis of datasets with a set of surface and IC markers to characterize the basophil response in controls and subjects allergic to peanut.
Figure 16C:
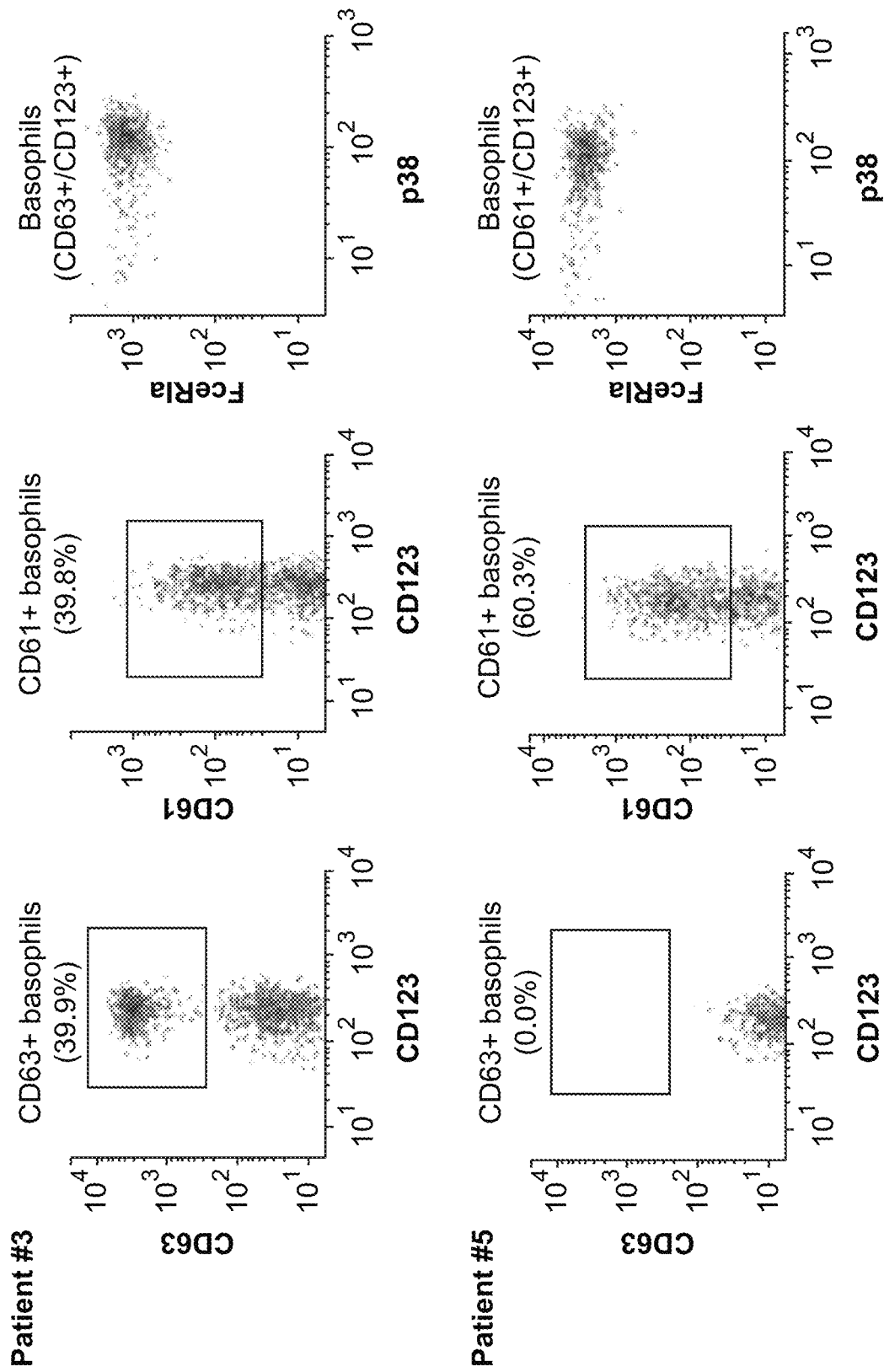

In the scenario of peanut allergy, a targeted analysis of activated basophils was performed of publicly available mass cytometry data (Q), comparing responses in patient and control subjects. The basophils were profiled for expression of CD61, CD63 and Fc epsilon RI a; and p38 MAPK activity. Subject-specific differences in response to PN allergen were identified based on the marker expression on the activated subset of basophils. The level of p38 MAPK activity in basophils expressing CD123 and Fc epsilon Ria was compared across individual controls and patient specimens along with CD61 and/or CD63 expression (FIG. 16A, FIG. 16B, and FIG. 16C).

The following results derived by multivariate analysis combining surface markers with IC phosphoproteins to collectively analyze the basophil response shed light on individual differences in basophil activation in allergic and control subjects:
1. The anti-IgE response was similar to PN response in the basophils of all allergic subjects.
2. Basophil CD63 expression was increased in 4/6 allergic subjects. In the other two subjects, increased CD61 expression was noted in response to PN and anti-IgE. In the four allergic subjects whose basophils upregulated CD63, the CD63+ subset of basophils expressed increased CD61 and p38 MAPK activity in response to PN and anti-IgE. In the other two subjects, the CD61+ fraction defined the subset of basophils with p38 MAPK response.
3. In response to anti-IgE, CD63 was not substantially upregulated in the basophils of 1/3 control and 2/6 allergic subjects, the latter showed higher pERK on basophils compared to the other 4 allergic subjects. However, CD61 expression was increased, confirming the basophil response. While basophils in none of the control subjects responded with increased CD61 or CD63 expression in response to PN, all allergic subjects had substantially increased CD61 and/or CD63 expression.
4. A fraction of basophils expressed increased p38 MAPK activity in allergic patients, in response to both anti-IgE and PN, irrespective of whether the basophils expressed CD63.

In conclusion, multivariate analysis of select markers on basophils shows that p38 MAPK activation and CD61 were consistently observed in the basophils of all allergic subjects in response to PN. Thus, including CD61 and p38 MAPK in flow-based allergy testing may improve the sensitivity of detecting basophil activation. This approach enables detection of cell-specific signaling biomarkers, and quantification of the level that may predict clinical symptoms, guide treatment, and predict response.

Data analysis can be performed by standard flow software that displays cells in bivariate dot plots or in high dimensional space through multivariate clustering, and can include automated classification. Data from each of the assay set-ups are not necessarily combined for analysis given different sample preparation methods impacting marker intensity and cell subset resolution, but are analyzed individually for eventual derivation of the phenotypic profile. Thus, manual analysis may be preferably utilized with software to analyze and interpret the data from each assay and to perform extrapolations from each assay analyzed individually and then in combination.

Methods and novel combinations of antibodies are provided for simultaneous quantitation of antigenic biomarkers in individual cells. Cell-based assays are provided to measure early, residual, or relapsed disease states for therapy guidance and to assess the biologic effects of ex vivo perturbations. Proteomic profiles that emerged from the data provided herein allow for prediction of therapeutic outcome and therapy responsiveness. Deregulated protein expression and activation profiles in certain cell-types (effector and memory T cells, neoplastic clones, NK cells, dendritic cells, etc.) of heterogeneous cellular mixtures (blood, bone marrow, mononuclear cells, body fluids, fine needle aspirates, core needle biopsy, etc.) are determined by a next-generation highly multiparametric cell analysis platform such as mass cytometry.

Using mass cytometry, a combination of markers was identified that is not routinely applied in diagnostics or for minimal residual disease identification. A larger number of cell-identification markers used simultaneously than what is typically done allowed identification of rare stem/progenitors of both myeloid and lymphoid lineages. Routine MRD analysis does not incorporate signaling markers, essentially critical functional activity markers of neoplastic cells. The limitations of fluorescence flow, as described above, have precluded routine analysis of signaling activity. In addition, signaling states are highly dynamic and must be captured within a certain window of time after sample collection. Typically, overnight shipment of a blood or marrow sample, as is routine practice for most commercial laboratories, is not suited for analysis of signaling networks in fresh state. However, fixing the sample soon upon collection can be a way to circumvent this issue.

Expression levels of certain regulatory proteins within key pathways of convergence in target cell populations can predict disease states, unravel therapeutic targets and provide guidance for clinical decision-making. These cell-based "biomarkers" can be various receptors and/or downstream effectors with key biologic functions such as maturation, proliferation, DNA repair, apoptosis, etc., and may react to stimuli such as hypoxia, oxidative stress, and external growth factors. In disease states, many normal functions are affected and can be measured by altered protein levels or activation states.

As such, biomarker profiling of signaling pathways can generate response signatures associated with certain disease states for risk-stratification and outcome prediction, enabling personalized care and drug discovery. Innovative combinations of antibodies were designed for identification of cellular subsets of biomarkers including multilineage tumor clones and immune cell subsets, and quantitation of selected signaling biomarkers for cell type-specific biologic behavior was performed. Cell type-specific proteomic signatures potentially associated with recurrence after stopping treatment were identified, resulting in a cost-effective cell-based prognostic assay. Further, blood analysis by cytometry for specific cell types allows for monitoring of therapy response, and prediction of off-therapy recurrence.

Cytokine induction can enhance detection of signaling activity particularly for cells that are not rapidly multiplying and have relatively low baseline activity. In routine phospho-flow analysis, cytokine induction is followed by fixation of cells. However, fixation can compromise the integrity of antibody-binding sites and can render suboptimal staining results. In addition, distinction between baseline and induced activity can be masked by high baseline activity preserved by immediate fixation and readily detectable. A method where sample is allowed to cool while staining allows for both staining of live cells with preservation of antibody-binding sites, and simultaneous capture of induced signaling activity while lowering of baseline activity.

The protocol described here for cytokine-induced testing of signaling states includes a pre-fixation surface staining method. This method may be used for cell-specific signaling network analysis to assess the biologic effects of ex vivo perturbations that modify downstream proteins in a way in which their expression or activity level changes. Often changes in one key protein leads to a cascade of changes in downstream proteins, which may have important functional significance. Thus, multiple functional readouts are feasible and are informative in pharmacoproteomic assays.

Data visualization strategies are necessary to build predictive and explanatory models from high dimensional data derived from cytometry assays to guide clinical management. The strategies allow selection of parameters based on variance in the dataset to generate correlative patterns associated with clinical situations such as medication non-adherence or resistance and may further predict effectiveness of targeted treatments for individual patients. The data plots displaying expression of signaling markers in different signaling pathways within individual cell types can create cell type specific patterns, allowing discovery of previously unknown correlations and cell-cell interactions. These are useful in communicating data to the medical and research community for optimal patient management.

Unless defined otherwise herein, all technical and scientific terms used herein have the same meaning as commonly understood by one of ordinary skill in the art to which this invention belongs. Singleton, et al., *Dictionary of Microbiology and Molecular Biology*, second ed., John Wiley and Sons, New York (1994), and Hale & Markham, *The Harper Collins Dictionary of Biology*, Harper Perennial, NY (1991) provide one of skill with a general dictionary of many of the terms used in this invention. Any methods and materials similar or equivalent to those described herein can be used in the practice or testing of the present invention.

The practice of the present invention will employ, unless otherwise indicated, conventional techniques of molecular biology (including recombinant techniques), microbiology, cell biology, and biochemistry, which are within the skill of the art. Such techniques are explained fully in the literature, for example, *Molecular Cloning: A Laboratory Manual*, second edition (Sambrook et al., 1989); Oligonucleotide Synthesis (M. J. Gait, ed., 1984; *Current Protocols in Molecular Biology* (F. M. Ausubel et al., eds., 1994); *PCR: The Polymerase Chain Reaction* (Mullis et al., eds., 1994); and *Gene Transfer and Expression: A Laboratory Manual* (Kriegler, 1990).

Numeric ranges provided herein are inclusive of the numbers defining the range.

Unless otherwise indicated, nucleic acids are written left to right in 5' to 3' orientation; amino acid sequences are written left to right in amino to carboxy orientation, respectively.

Definitions

"A," "an" and "the" include plural references unless the context clearly dictates otherwise.

"Mass cytometry" refers to a single-cell multiparametric protein detection technology. Antibodies are tagged with isotopically pure rare earth elements, allowing simultaneous measurement of greater than 40 parameters while circumventing the issue of spectral overlap which is observed with fluorophores. The multi-atom metal tags are ionized, for example by passage through an argon plasma, and then analyzed by mass spectrometry. See, e.g., Bandura et al. (2009) *Analytical Chemistry* 81(16):6813-6822; Ornatsky et al. (2010) *Journal of Immunological Methods* 361(1-2): 1-20; Bendall et al. (2011) *Science* 332(6030):687-696.

"SPADE" refers to "Spanning-tree Progression Analysis of Density-normalized Events." SPADE clusters phenotypically-similar cells into hierarchy that allow high-throughput, multidimensional analysis of heterogeneous samples. See, e.g., Qiu et al. (2011) Nat. Biotechnol. 29(10): 886-91.

"Phospho-flow" or "phos-flow" analysis refers to use of FCM to analyze phosphorylated IC molecules at the single cell level, such as, for example, phosphorylated signaling proteins and cytokines.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact full-length antibodies, but also fragments thereof (such as Fab, Fab', F(ab')$_2$, Fv), single chain (ScFv), mutants thereof, fusion proteins comprising an antibody portion, and any other modified configuration of the immunoglobulin molecule that comprises an antigen recognition site of the required specificity. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

A "monoclonal antibody" refers to a homogeneous antibody population wherein the monoclonal antibody is comprised of amino acids (naturally occurring and non-naturally occurring) that are involved in the selective binding of an antigen. A population of monoclonal antibodies (as opposed to polyclonal antibodies) is highly specific, in the sense that they are directed against a single antigenic site. The term "monoclonal antibody" encompasses not only intact monoclonal antibodies and full-length monoclonal antibodies, but also fragments thereof (such as Fab, Fab', F(ab')$_2$, Fv), single chain (ScFv), mutants thereof, fusion proteins comprising an antibody portion, and any other modified configuration of the immunoglobulin molecule that comprises an antigen recognition site of the required specificity and the ability to bind to an antigen (see definition of antibody). It is not intended to be limited as regards to the source of the antibody or the manner in which it is made (e.g., by hybridoma, phage selection, recombinant expression, transgenic animals, etc.).

"Fv" is an antibody fragment that contains a complete antigen-recognition and binding site. In a two-chain Fv species, this region consists of a dimer of one heavy and one light chain variable domain in tight, non-covalent association. In a single-chain Fv species, one heavy and one light chain variable domain can be covalently linked by a flexible polypeptide linker such that the light and heavy chains can associate in a dimeric structure analogous to that in a two-chain Fv species. It is in this configuration that the three CDRs of each variable domain interact to define an antigen-binding specificity on the surface of the VH-VL dimer. However, even a single variable domain (or half of a Fv comprising only 3 CDRs specific for an antigen) has the ability to recognize and bind antigen, although generally at a lower affinity than the entire binding site. A "Fab" fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge regions.

A "specific binding member" relates to a member of a receptor/ligand specific bind pair that has specific affinity for each other, such as but not limited to antibody/antigen, receptor/ligand and the like. Included are active fragments or functional fragments, which would include active domains, such as in the case of antibodies the Fv region. In many instances, antibody and specific binding member are used interchangeably.

A "subject" can be a human or non-human, including animals, companion animals, agricultural animals, and test animals.

A "disease, disorder, or condition" can be any affliction of a subject, be it life threatening to an annoyance, or "silent" as not noticed by the subject.

An epitope that "specifically binds" or "preferentially binds" (used interchangeably herein) to an antibody is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to an epitope is an antibody that binds this epitope with greater affinity, avidity, more readily, and/or with greater duration than it binds to other epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

A "variable region" of an antibody refers to the variable region of the light chain or the variable region of the heavy chain, either alone or in combination.

"Complementarity determining region" (CDR) refers a relatively short amino acid sequence found in the variable regions of antibody molecules. The CDRs contain amino acid residues that determine the specificity of antibody molecules and make contact with a specific antigen.

Methods for Assessing Ex Vivo Perturbations of Cell Populations

Methods are provided for assessing effects of ex vivo perturbations on signaling pathways in cells of mixtures, such as heterogeneous biologic mixtures.

The disclosed methods may be used for analysis of alterations in regulatory proteins and their activation status due to external perturbations. For example, the method may be used in conjunction with phos-flow analysis of phosphorylation states.

In some embodiments, the method is a modification of standard phos-flow approach (e.g., where the cells are stained post-fixation and there is no cooling step prior to fixation). In contrast, the methods disclosed herein allow exaggeration of biologic effects due to external stimuli by cooling the sample, which quenches baseline (pre-stimulation) activity levels. Levels of certain biomarkers within modified signaling networks are determined in cell-types of interest. The data capture platform is a highly multiplexed cell analysis platform such as a mass cytometer.

A mixture of cells (e.g., a heterogeneous mixture of cells, such as blood, bone marrow, body fluids) is exposed to an exogenous stimulus (such as interleukins or hormones) that alters signaling, +/−an inhibitor that potentially alters cellular responses to modulators. The exogenous stimulus may include, but is not limited to, IL3, IL6, IFN☐2, PMA, ionomycin, IFN-g, LPS, interleukins, SCF, FLT3L, GM-CSF, G-CSF, EPO, and/or TPO. The modified sample is then reacted with antibodies that bind to cell surface biomarkers, such as lineage-associated and other surface markers on ice. No stimuli (constitutive signaling) or drug inhibitor+stimulator(s) may also be assessed. The sample is then fixed and permeabilized, and further reacted with antibodies towards IC markers.

The method may be conducted as follows:
1. The sample is exposed to one or more modulator(s) at a first temperature (e.g., 37° C.).
2. The modulated sample is then contacted with a panel of antibodies directed towards surface antigens at a second temperature that is lower than the first temperature (e.g., 0° C., for example, on ice).
3. The sample is subjected to fixation and permeabilization and is contacted with a panel of antibodies that bind IC antigens.
4. Data is captured on a multiparametric cell analysis platform and analyzed further using flow analysis and high-dimensional data analysis algorithms. Thus, comprehensive biomarker response profiles are generated for cell-specific effects of signaling modulators and test compounds.

In Example 1, lowering of baseline and more dramatic fold-change with the pre-fixation method disclosed herein is demonstrated, compared to the traditional post-fixation staining approach. The individual subpopulations are better delineated in the pre-fixation staining approach due to better preservation of surface epitopes.

Fixation of the cells may be performed with any reagent that is suitable for inactivation of enzymes, including but not limited to kinases, phosphatases, and proteases, in order to "fix" the in vivo state of phosphorytlation. In some embodiments, a paraformaldehyde-based fixative is used, such as Phosflow Lyse/Fix buffer, available from BD. In some embodiments, a formaldehyde-based fixative is used. Permeabilization of cells may be performed, for example, with an organic solvent, a detergent such as Triton X-100, or saponin. In some embodiments, fixation and permeabilization are performed simultaneously. In other embodiments, fixation and permeabilization are performed sequentially. In other embodiments, cells are not fixed but cooled and further analysis of a modified cell state is performed of live cells.

The methods described herein may be deployed with any suitable multiparametric cell analysis technique, including but not limited to, mass cytometry, multiplexed fluorescent flow FCM, multiplexed immunohistochemistry, immunocytochemistry, and multiplexed qRT-PCR, e.g., any technique that is capable of use for quantification of single cell expression of a combination of analytes. Readout(s) may include any post-translational modification due to a disease state (e.g., oncogenic disease state) or induced perturbed state, including, but not limited to, phosphorylation or acetylation.

In some embodiments, staining of a sample such as whole blood prior to fixation eliminates two wash steps which would have to be performed to remove fixative if fixation were performed prior to staining.

In some embodiments, some residual phosphatase activity during the cooling step may cause dephosphorylation, so the absolute level of phosphoproteins may be lower than observed in a post-fixation staining method.

Combinations of Cellular Markers for Multiparametric Analysis of Cell Populations Combinations of cellular markers and antibodies directed thereto are disclosed herein, which may be used, for example, for prognostic evaluation, outcome prediction, and therapy guidance in disease states. Combinations of antibodies disclosed herein may be used for simultaneous quantitation of antigenic biomarkers in individual cells.

Cell type-specific protein expression profiles that emerge from analysis of data generated for the combinations of biomarkers disclosed herein may allow for outcome prediction and therapy responsiveness. Deregulated protein expression and activation profiles in certain cell-types of cellular mixtures, such as heterogeneous cellular mixtures (e.g., blood, bone marrow, mononuclear cells, body fluids, fine needle aspirates, core needle biopsy, etc.) may be determined by highly multiparametric cell analysis platforms such as mass cytometry.

Combinations of antibodies are disclosed herein for identification of cellular subsets such as tumor sub-clones and immunologic subsets, and quantitation of selected biomarkers for cell-specific biologic behavior. Biological features associated with unfavorable clinical factors may be identified leading to further research and development of cost-effective prognostic assays. For example, activated signaling networks in therapy-resistant subpopulations can guide further therapy by identifying survival pathways that can be more specifically targeted.

Antibodies directed to the following combination of biomarkers identified stem/progenitor cell subpopulations in the peripheral blood of a patient previously treated for chronic myelogenous leukemia who had been off therapy for 2 months: CD4-145Nd, CD20-147Sm, CD15-148Nd, CD7-149Sm, CD3-150Nd, CD123-151Eu, CD27-152Sm, CD45RA-153Eu, CD45-154Sm, CD19-156Gd, p-p38-157Gd, CD127-158Gd, CD11c-159Tb, CD14-160Gd, IgD-161Dy, p-ERK1/2-162Dy, IKBtot-163Dy, pSTAT3-164Dy, pS6 kinase-165Ho, CD16-166Er, CD38-167Er, CD24-168Er, CD117-169Tm, CD8a-170Er, CD66-171Yb, pSTAT5-172Yb, CD34-173Yb, HLA-DR-174Yb, CD56-175Lu, CD33-176Yb. In Example 2, a unique combination of markers, including CD3, CD19, CD34, CD45, KIT/CD117, and CD127/IL-7R identified therapy-refractory subpopulations with activated p-STAT5 and p-38 MAP kinase, which could together or in part indicate recurrent CML. This combination of markers allows for cell-specific biomarker assessment that is of prognostic and therapeutic relevance.

In various embodiments, combinations of antibodies directed to subsets of the biomarkers disclosed above may be used for analysis of various cell populations and samples, for analysis of disease states, determination of cell lineage and/or maturation, prediction of therapeutic outcomes, and/or analysis of therapeutic effectiveness.

A first aspect of the present invention includes a composition, including: a) a combination of specific binding members comprising a detectable label, including: 1) at least one identified cell surface specific binding member that specifically binds with at least one cell surface antigen, and 2) at least one identified IC specific binding member that specifically binds with at least one IC antigen; and b) a physiological acceptable carrier; where the specific binding members can specifically bind with and identify one or more clinically relevant cell types in a biological sample including cells from a sample from subject having or suspected of having at least one disease, disorder, or condition; and further where the composition of matter can label and identify cell populations relating to the disease, disorder, or condition.

In another aspect of the present invention, the specific surface binding members, the IC specific binding members, or a combination thereof, are conjugated with a detectable label.

In a further aspect of the present invention, the specific binding member is an antibody, a receptor, a ligand, an active fragment of any of the foregoing, or a combination thereof.

In an additional aspect of the present invention, the biological sample is blood, bone marrow, needle aspirates, tissue biopsies, or a combination thereof.

In another aspect of the present invention, the disease condition is an allergy, a peanut allergy, autoimmune condition, neoplastic states diagnosed as hematopoietic stem cell neoplasms (CML, de novo acute myeloid leukemia, acute myeloid leukemia arising from a myelodysplastic syndrome or a myeloproliferative neoplasm) or lymphoma, and immune-mediated conditions resulting in immune cell infiltrates.

In a further aspect of the present invention, the detectable label is at least one fluorescence or other label that can be detected in a multiparameter single cell detections system.

In an additional aspect of the present invention, the combination of specific binding members specifically bind with p-STAT5, p-p38 MAPK, and/or p-CRKL, or a combination thereof, and the disease condition is leukemia, including CML.

In another aspect of the present invention, the combination of specific binding members additionally bind with p-STAT5$^{hi}$ cell subsets to differentiate cell subsets, based on expression of surface markers including those defining cell immaturity (CD34) or lineage commitment (CD3, CD19); and receptors comprising KIT, IL3R, IL7R, and CD45, that activate downstream signaling pathways.

In a further aspect of the present invention, the combination of specific binding members specifically bind with at least, p-p38MAPK and p-ERK as markers of activated basophils, or a combination thereof; and the disease condition is a food allergy, comprising peanut allergy.

In an additional aspect of the present invention, the combination of specific binding members additionally bind with pp38 MAPK$^{hi}$ cells to distinguish cells based on expression of and presence or absence of or expression level of lineage-associated markers that comprise CD45 and CD123 and platelet adhesion and degranulation markers that comprise CD61 and CD63 to distinguish patient subgroups with p-p38MAPK+/CD63– or p-p38MAPK+/CD63+ basophils.

A second aspect of the present invention includes a method of designing of panels of specific binding members to analyze expression levels of functional cell surface proteins on a collection of live cells from a subject having an identified disease, disorder, or condition, including: a) fixing a first portion of said collection of live cells to capture activated states of said cells in a fixed state to form a fixed portion of cells; b) not fixing a second portion of said collection of live cells to form a live portion of cells; c) using the composition of claim 1 to determine overall binding profiles of specific binding members to said fixed portion of said cells and said live portion of cells; where the overall binding profiles can be used to identify a cell subset based on expression profile of surface and IC markers that are present in the compositions of the present invention.

In another aspect of the present invention, the identification and profiling of clinically relevant cell types by two or more distinct cell preparation methods that best preserve the integrity of tested markers are identified.

In a further aspect of the present invention, additional markers on live cells to identify other immune cell types, such as particular subsets of T and NK cells, of prognostic, clinical, or a combination thereof relevance are utilized.

In an additional aspect of the present invention, ultimate derivation of cell profile based on analysis of data derived by samples analyzed by both or all methods applied for optimal assessment of surface and IC marker expression.

A third aspect of the present invention includes a combination of specific binding members directed to cellular biomarkers for identification of cells that have abnormally high signaling activities including: where the specific binding members are directed to a set of biomarkers from, and added to, the following first-pass single-tube mass cytometry panel, in order to minimize the marker set to the markers with discriminative value: CD3, CD4, CD8a, CD11c, CD14, CD16, CD19, CD33, CD34, CD38, CD45, CD56, CD66, KIT/CD117, IL3R/CD123, p-p38 MAPK, total IKB, p-STAT3-164Dy, p-STAT5-172Yb, and pS6 kinase; and where the specific binding members are combined in the two- or three- (or more)-tube FCM configuration to target the analysis to cell types relevant in characterizing particular disease states, treatment response, and mechanism of relapse.

In another aspect of the present invention, the combination of specific binding members of the present invention include surface specific binding members directed to cell surface receptor proteins comprising CD117/KIT, CD123/IL3R, CD127/IL7R; and IC phospho-specific binding members towards activated proteins phosphorylated STAT3, STAT5, and p38 MAPK, S6 kinase, and ERK 1/2, for functional analysis of cell types based on their signaling activation profile of cell survival pathways.

In a further aspect of the present invention, the combination of specific binding members of the present invention include where each different specific binding member comprises a different metal tag or other reporter molecule.

A fourth aspect of the present invention includes a method of predicting the cause of disease relapse, guiding disease therapy, and/or predicting disease outcome in a subject, including the steps: a) labeling an aliquot from the cell sample with surface antibodies only; b) contacting a sample that contains a population of cells with one or more reagents that fixes and permeabilizes the sample, thereby producing a fixed and permeabilized cell population; c) contacting the fixed and permeabilized cell population with a combination of specific binding members that are directed to cellular biomarkers, where the specific binding members are directed against surface and IC biomarkers selected from a first-pass single tube panel comprising CD3, CD4, CD8a, CD11c, CD14, CD16, CD19, CD33, CD34, CD38, CD45, CD56, CD66, KIT/CD117, IL3R/CD123, p-p38 MAPK, p-ERK 1/2, total IKB, p-STAT3, p-STAT5, and p-S6 kinase;
d) identifying one or more subsets of cells with abnormally high signaling activities as assessed by one of the binding members, wherein the resulting subset is a cell type and is indicative of disease relapse/recurrence or other outcome in the subject.

In another aspect of the present invention, the specific binding members are directed to surface receptor or receptor type proteins comprising KIT, FLT3, IL3R, IL7R, CD45; and IC signaling proteins comprising p-STAT5, p-STAT3, p-p38 MAPK, p-ERK 1/2, and p-S6 kinase.

In a further aspect of the present invention, the identifying one or more subsets within the cell mixture based on abnormally high expression of activated proteins based on phosphorylation of such proteins on one more amino acids, wherein said activated proteins comprise p-STAT5, p-STAT3, p-p38 MAPK, p-ERK 1/2, and p-S6 kinase.

In an additional aspect of the present invention, the single cell analysis method includes multiparametric protein or other antigenic analyte expression analysis, comprising cytometry.

In another aspect of the present invention, each different specific binding member includes a different metal tag or reporter molecule with panel configuration compatible with the instrument on which samples are analyzed, while satisfying the aim of target cell identification, characterization, and quantification.

In a further aspect of the present invention, the aliquot of cell mixture that is modulated for effect of targeted stimulation or inhibition of certain cells within the mixture is done so with at least one modulating substance prior to contacting the sample with one or more reagents that fixes and permeabilizes the sample.

In an additional aspect of the present invention, at least one modulating substance includes at least one cytokine or growth factor or inhibitor.

In another aspect of the present invention, at least one modulating substance includes IL3, IL6, IL7, IFNa2, EPO, and G-CSF; with or without the addition of an inhibitor of a signaling or other biochemical pathways or cell process.

In a further aspect of the present invention, the sample that contains a population of cells includes a cell line, fresh or frozen mononuclear cells, a fresh human sample, a fresh human sample in a preservative, or a tissue sample selected from blood, marrow, fine needle aspirate, and a tissue biopsy sample.

The following examples are intended to illustrate, but not limit, the present disclosure.

EXAMPLES

Example 1

Materials and Methods

A fresh whole blood sample from a 54-year-old adult male patient with chronic-phase chronic myelogenous leukemia (CML) who presented with neutrophilic leukocytosis with a total WBC: 33.3 K/□l (PMN: 17.98 K/□l, Lymphocytes: 3.66 K/□l, Monocytes: 0.33 K/□l, Eosinophils: 0.67 K/□l, Basophils: 4.0 K/□l, immature granulocytes: 6.3 K/□l, Blasts: 0.33 K/□l), Hb: 15.8 g/dL, Hct: 47.9%, and PLT: 536 K/□l was obtained from UCSF Helen Diller Family Comprehensive Cancer Center with informed consent. Cell-specific cytokine-induced effects in the leukemic v. normal state were compared. The sample was exposed to: IL3 (50 ng/ml), IL6 (50 ng/ml), IFN□2 10,000 IU/ml or no stimulus, for 15 min at 37° C.

Using the pre-fixation surface staining method, the modulated samples were then contacted with a cocktail of antibodies towards surface antigens for 15 minutes on ice, followed by fixation with Phosflow Lyse/Fix reagent (BD Biosciences, San Jose, Calif.) 10 minutes at 37° C., and washed 2× with "wash buffer" (PBS 0.1% BSA, 2 mM EDTA, 0.05% azide) by centrifugation at 500×g for 5 minutes.

Using post-fixation surface staining, a set of patient and healthy control samples was fixed immediately after the cytokine stimulation with BD Phosflow lyse/fix reagent for 10 min at 37° C. and washed 2× in wash buffer, followed by surface staining for 30 minutes at room temperature and washed 2× with wash buffer.

A panel of 27 metal-tagged antibodies was constructed using Maxpar polymers and lanthanide metals as per the manufacturer's conjugation protocol (DVS Sciences, CA). Surface staining was performed with the following antibodies against 1) lineage-determining antigens: CD8a-144Nd, CD4-145Nd, CD20-147Sm, CD16-Nd148, CD45-154Sm, CD11c-159Tb, CD14-160Gd, CD33-166Er, CD24-168Er, CD3-170Er, CD66-171Yb, CD56-175Lu; 2) activation- and maturation-associated antigens: CD27-152Sm, CD45RA-153Eu, IgD-161Dy, CD38-167Er, HLA-DR-174Yb, CD25-176Yb; and 3) cytokine receptors: IL3R/CD123-151Eu. After 2× wash in wash buffer, both sample sets (prepared by pre-fixation and post-fixation surface staining methods) were resuspended and permeabilized with 100% methanol, washed 2× in wash buffer, and labeled for analysis of select IC antigens using the following antibody conjugates: pp38 MAPK-157Gd, total IKB□-163Dy, pSTAT3-164Dy, pSTAT1-169Tm, pSTAT5-172Yb, pPLC□2-173Yb. After 1× wash, the samples were treated with DNA Iridium intercalator for a final concentration of 1:2000. The data were captured by inductive coupled time-of-flight cytometry (CyTOF) and analyzed by traditional gating tools and high dimensional data analysis algorithms including Spanning Tree Progression of Density Normalized Events (SPADE).

Results

As compared to normal cell counterparts in the healthy control sample, CML cells in chronic phase had the following features:

A marked potentiated effect of IL3 on p-STAT5 in CML cells of myeloid lineage (neutrophils, monocytes, and basophils) was observed compared to majority of the lymphocytes in CML, rendering IL3-STAT5 a putative marker of neoplastic myeloid cells and possibly BCR-ABL positivity. IL6-STAT3 in CD4 T cells and monocytes likely represent immune response in CML (FIGS. 1 and 2).

Figure 3:
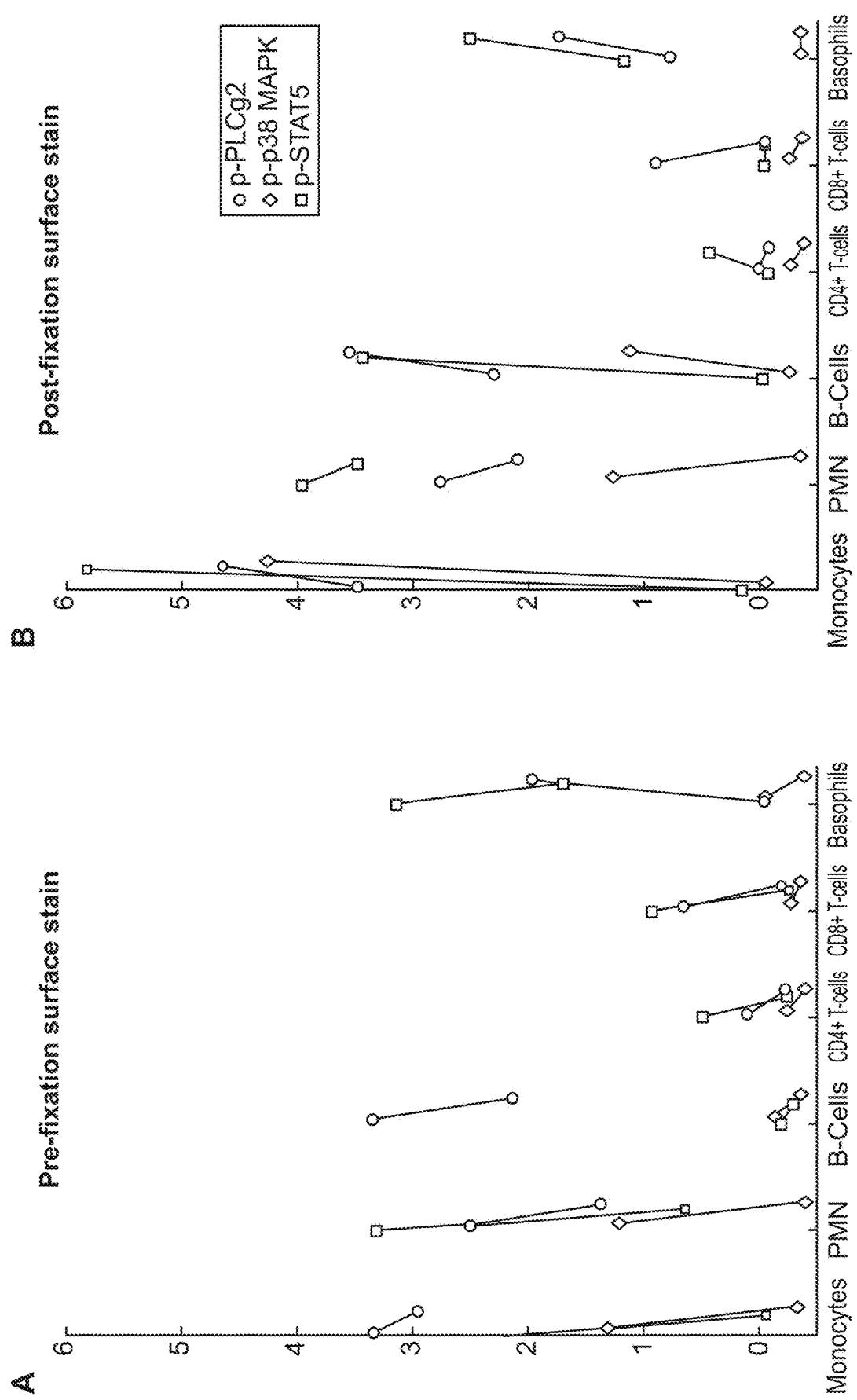
FIG. 3 illustrates baseline activities for selected cell-types (a. monocytes, b. neutrophils, c. B cells, d. CD4 T cells, e. CD8 T cells, f. Basophils) and IC protein readouts (p-STAT5, p-p38 MAPK, and p-PLCg2) in patient compared to control, comparing pre-fixation and post-fixation staining methods. Baseline activities are lower by pre-fixation method where cooling the sample (while staining for surface markers) causes enzyme inactivation thus lowering baseline activities with a prominent effect in patient cells compared to normal possibly due to more labile factors in the metabolically active patient cells.

Baseline signaling activity levels were more prominent in post-fix surface staining methods due to preservation of signaling activity through fixation. By pre-fixation surface staining, all patient cells had lower baseline than control, except pPLC□2 readout in Basophils. Thus, pre-fixation surface staining caused lowering of baseline IC readouts in patient cells, suggestive of quenching of baseline phosphorylation possibly due to inactivation of enzymatic activity during cooling, with relative preservation of effects due cytokine induction. By post-fixation surface staining, CML monocytes, B-cells, and basophils have higher baseline than control, consistent with capture of high baseline activities in active state due to fixation prior to staining. CML PMNs had lower baseline compared to control (possibly due to reduction of STAT5 activity due to apoptosis). Slightly higher baseline p-STAT5 in CD4 T cells suggests admixed clonal CML T cells in the CD4 T cell subset (FIG. 3).

Figure 4:
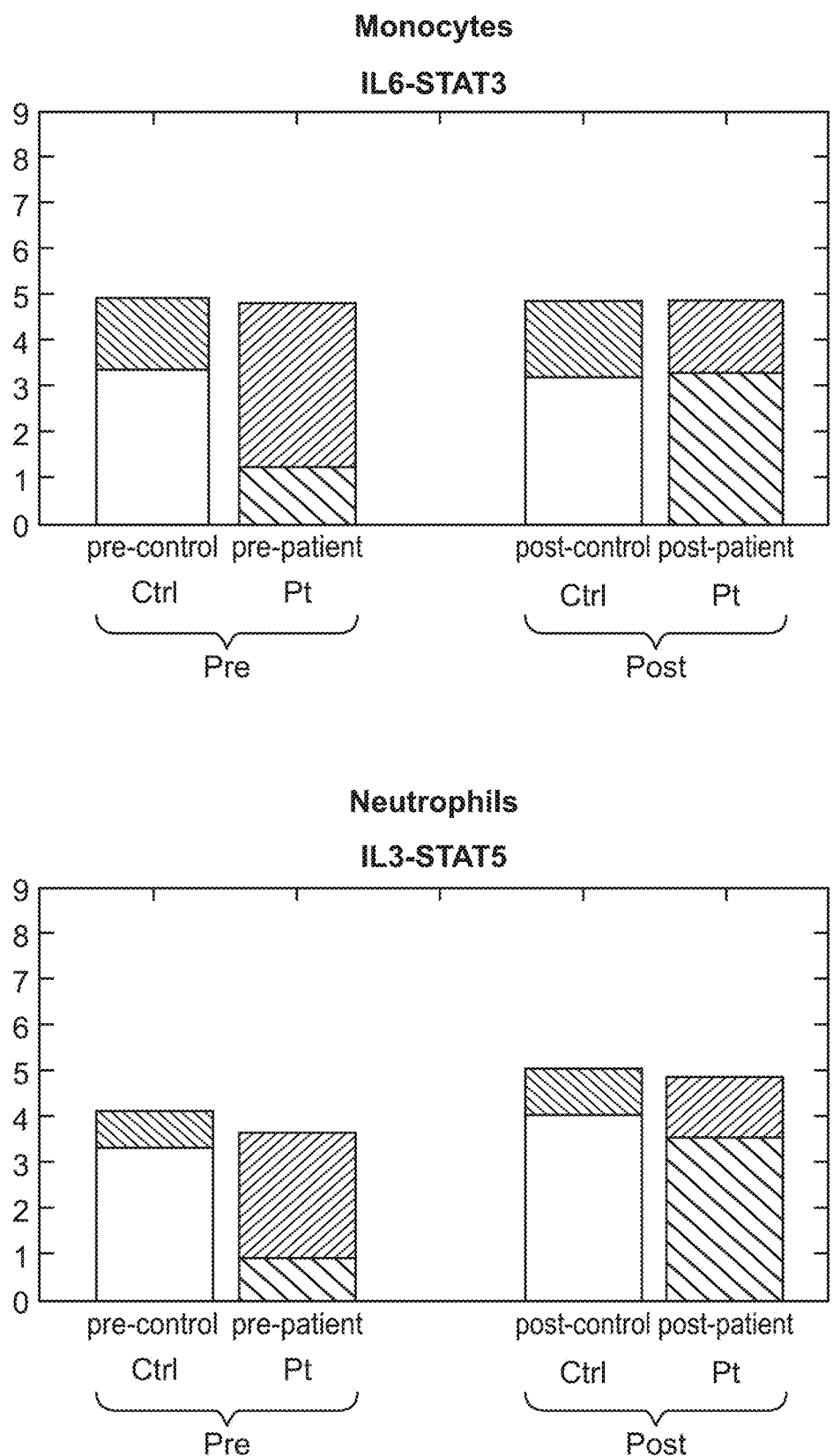
FIG. 4 illustrates lower baseline activities (represented by area below the dividing line in each bar) in patient cells compared to control cells, while the fold change (represented by area above the dividing line in each bar) is higher in patient cells compared to control cells using the pre-fixation method, while the post-fixation method failed to reveal a notable difference between induced change in the patient and healthy control cells.
Figure 7:
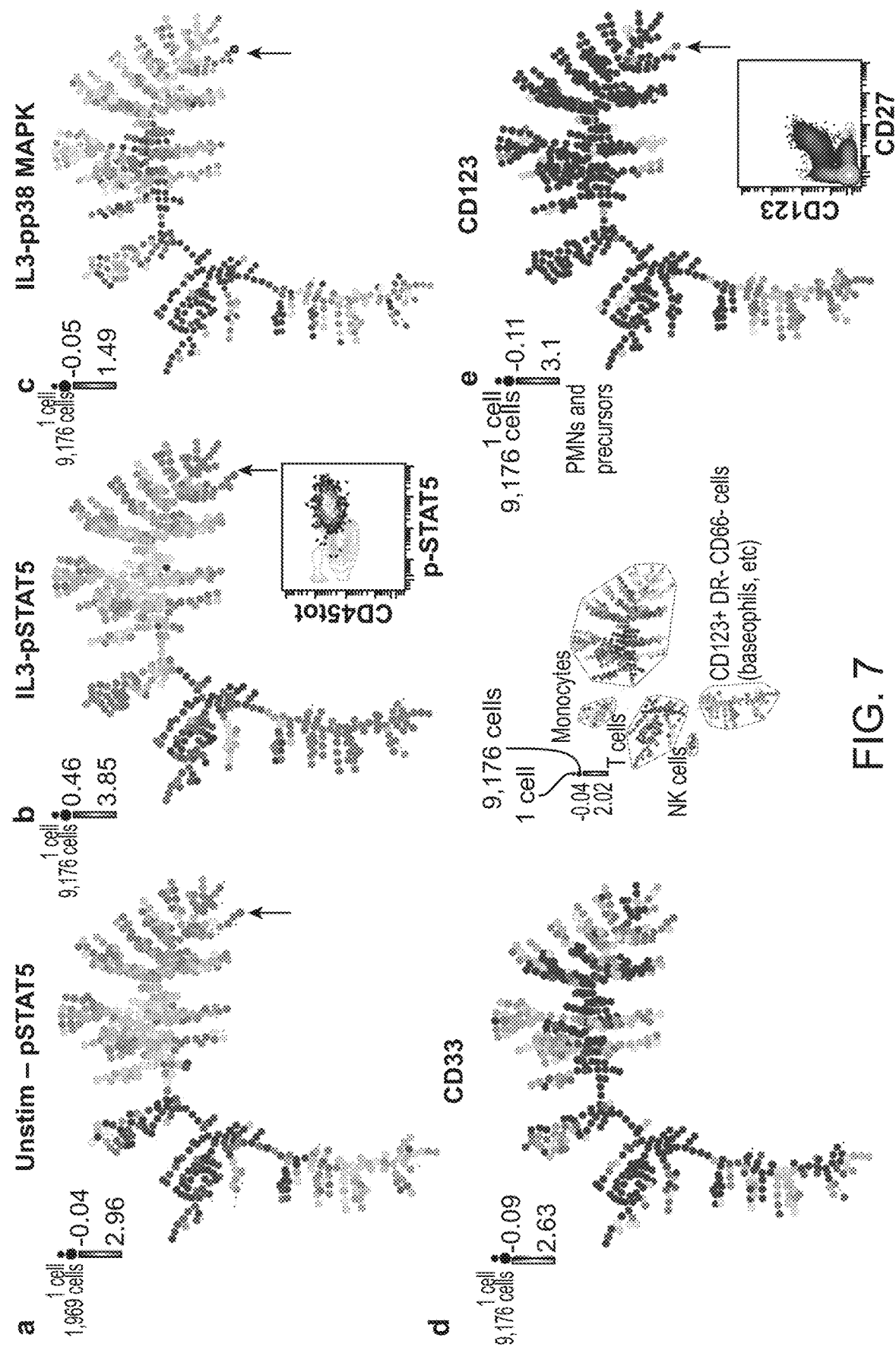
FIG. 7 shows SPADE analysis of all cells, arrow points to rare CD33+/IL3R+ cells that have high baseline and IL3-induced activity.

Fold-change ($\log_{10}$ induced–$\log_{10}$ basal) representing differential in the baseline and induced activity was higher in the pre-fixation surface staining method, possibly due to relative preservation of induced activity while quenching of baseline activity level due to enzyme inactivation in the cooling step. Elevated IL3-p-STAT5 in myeloid cells, and IL6-p-STAT3 in monocytes was observed in CML compared to healthy control cells when tested using the pre-fixation method as compared to the post-fixation method (FIG. 4). Thus, pre-fixation surface staining can unravel subtle post-translational modifications (which may be masked due to high baseline activity or poor preservation of low density lineage-associated surface antigen epitopes in the post-fixation staining method) induced due to ex vivo perturbations. Also, CD33+ subset was not as well distinguished in the post-fixation surface staining method due to non-specific and lowering intensity of the CD33 signal (FIG. 7).

Differential cytokine-induced activity in CML cells based on stage of maturation with less differentiated (or multipotent progenitors) having lower growth factor responsiveness than more differentiated cells. Growth factor responsiveness could thus correlate with response to enzyme-targeted therapies that inhibit receptor-mediated signaling pathways.

Figure 5:
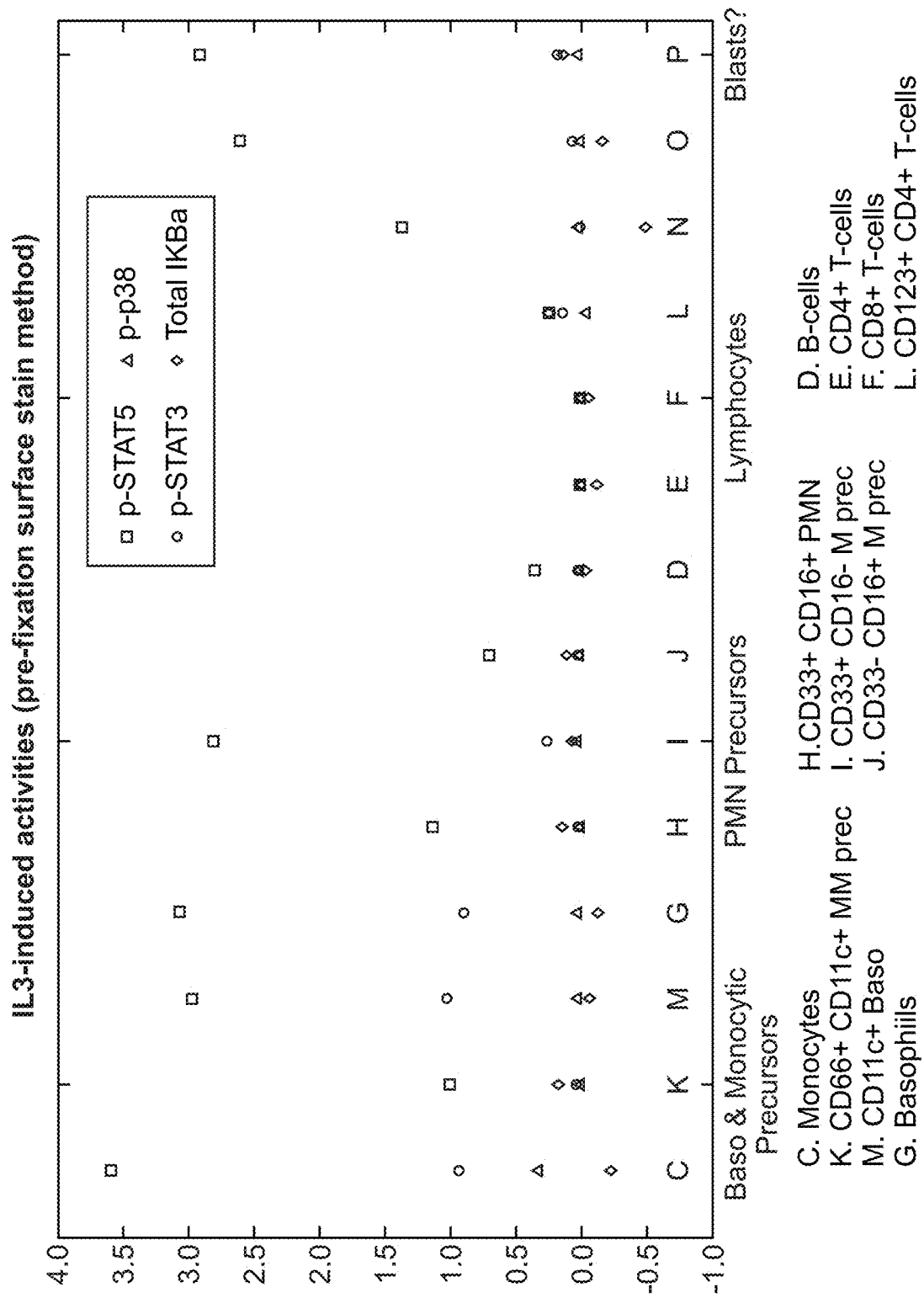
FIG. 5 illustrates cell type-specific activities in select IC protein readouts due to IL3 induction. The analysis is based on pre-fixation data due to better signal to noise ratio for CD33 antigen expression. IL3-induced p-STAT5 and p-STAT3 activities in CML clonal cells appear to be correlated with CD33 and possibly CD123 expression.

Delineation of $CD33^{hi}$ and $CD33^{lo}$ cells, performed by extracting cell subsets from the pre-fixation surface staining data set, demonstrated correlation between CD33 and IL3-STAT5 activity (FIG. 5).

Figure 6:
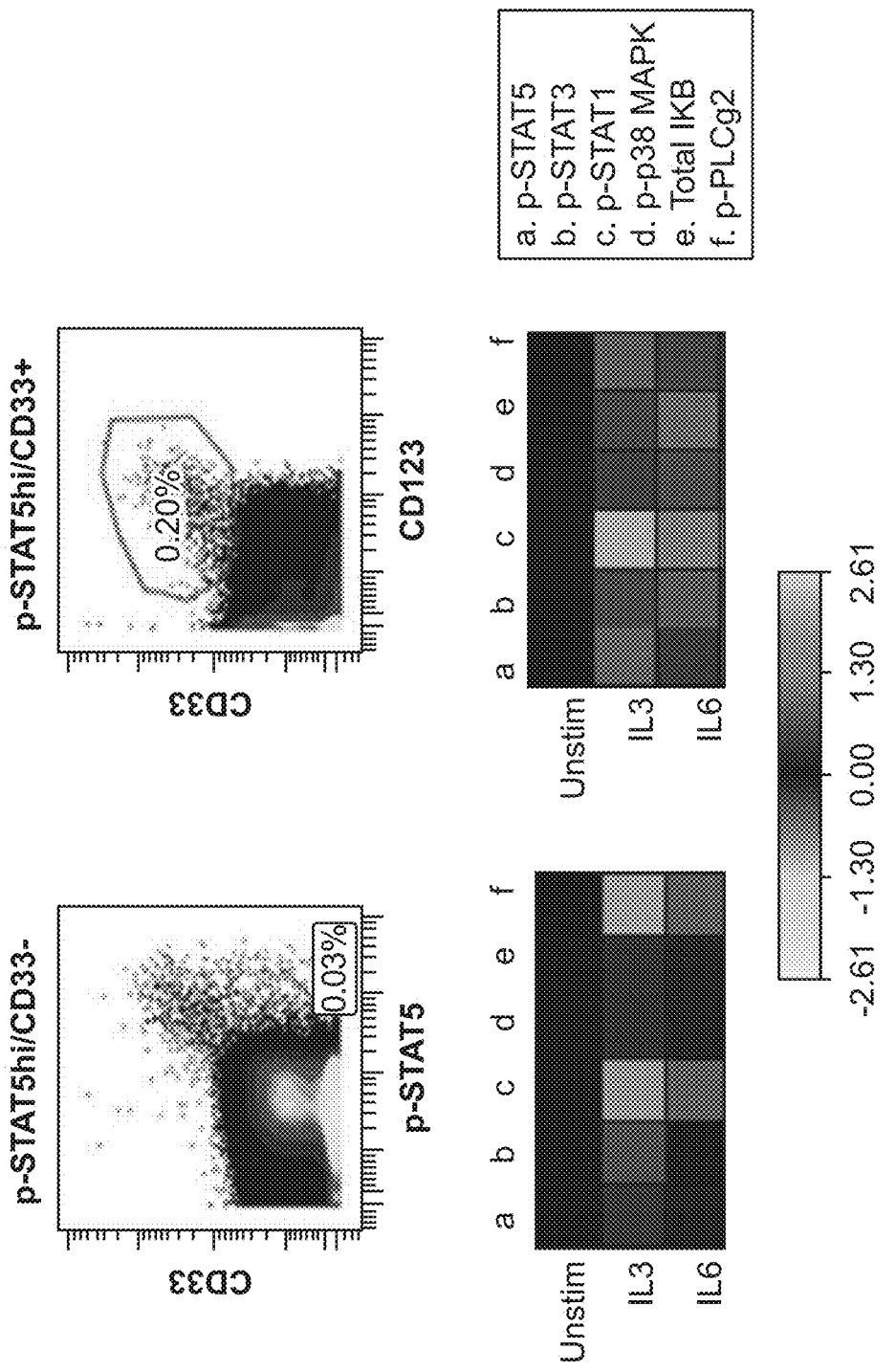
FIG. 6 illustrates differential induced STAT5 activities in CD33+ and CD33− cells gated by using p-STAT5 v. CD33, and CD33 v. CD123 bivariate plots. The CD33− undifferentiated CML stem/progenitor cells had lower IL3- and IL6-induced upregulation compared to more differentiated cells, possibly due to constitutive activity, with lower reliance on cytokines from the inflammatory milieu.

Lower IL3- and IL6-induced STAT5 responses in CD33– multipotent CML stem/progenitor cells (with high baseline p-STAT5 activity) (FIG. 6), suggests lower growth factor responsiveness (presumably due to BCR-ABL independent signaling activity) in treatment-refractory stem/progenitor cells. Thus cytokine-induced STAT5 activity could be a marker for tyrosine kinase inhibitor responsiveness useful for drug screening assays. Thus, drugs that increase the cytokine-response in stem/progenitor cells could be of therapeutic benefit in treated relapsed/refractory disease.

A minute CML myeloid progenitor cell subset (0.52%) with both high baseline and IL3-induced p38 MAPK and -pSTAT5 activities (relative to more mature myeloid cells) associated with CD27 and IL3R/CD123 expression in these cells (FIG. 7).

Figure 8:
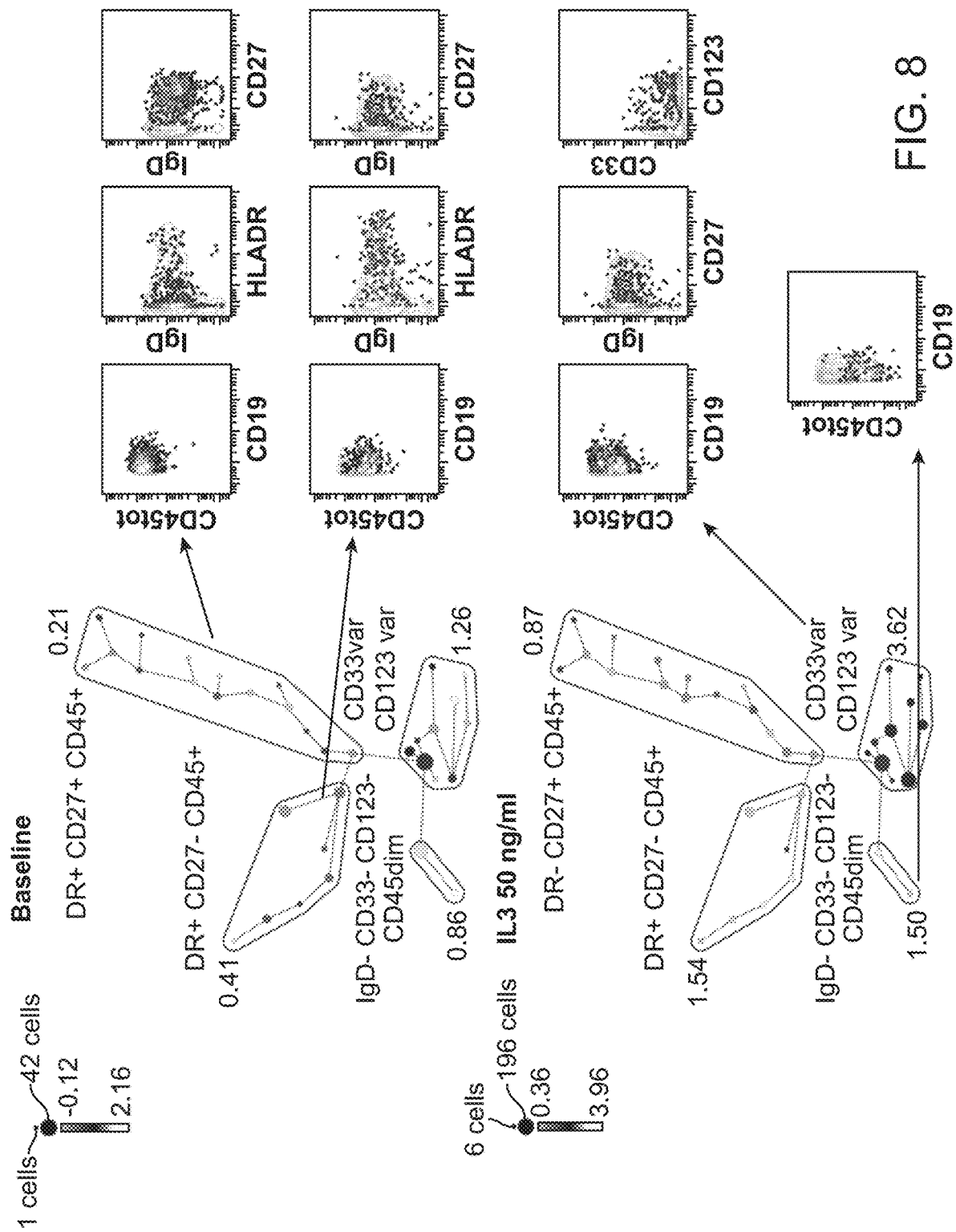
FIG. 8 shows SPADE analysis of CD19+ cell fraction, capturing cells co-expressing CD33 and/or IL3R cells with high baseline and IL3-induced p-STAT5 activity, suggesting admixed multipotent progenitor cells with high IL3-STAT5. More mature B cells lack significant p-STAT5 activity.
Figure 9:
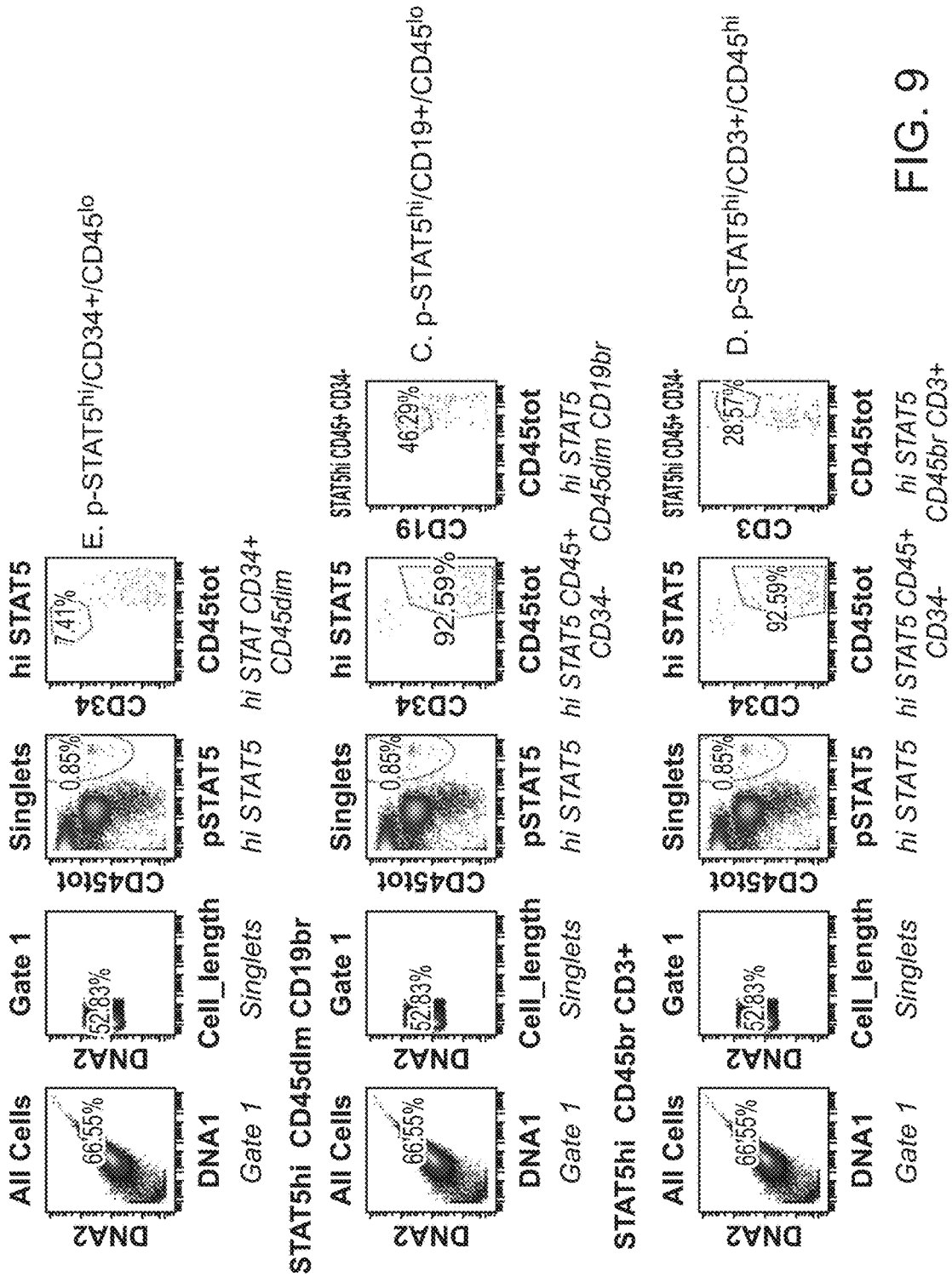
FIG. 9 shows identification of cells with high p-STAT5 activity in the patient sample with relapsed CML, and illustrates gating strategy used to identify the lineages of p-STAT5$^{hi}$ cells. Cells with high p-STAT5 activity levels were identified on CD45 v p-STAT5 bivariate plot. After identifying the CD34+ cells on CD34 v. CD45 plot, CD19 v. CD45 and CD3 v. CD45 plots were used for lineage identification of more differentiated CD34− or CD34$^{lo}$ cells. p-STAT5$^{hi}$ cells comprised of a mixture of CD19+/CD45$^{lo}$ and CD3+/CD45+ lymphoid progenitors and rare CD34+/CD45$^{lo}$ progenitor/stem cells.

The minute CD19+ cell subsets had higher baseline and IL3- and IL6-induced STAT5 activity when co-expressing CD33 or CD123 myeloid markers, potentially representing cells that are derived from the BCR-ABL (+) CML clone (FIG. 8). Similar cells could possibly be identified through experimentation in other BCR-ABL+ leukemia (including forms of precursor B lymphoblastic leukemia and biphenotypic leukemia). Thus, CD19+/CD33+ and/or CD19+/CD123+ cells with activated STAT5 networks likely represent clonal BCR-ABL (+) cells in Ph+ leukemia, and CD19+ cells that are CD123+ or CD33+ and p-STAT5$^{hi}$ could be used for cell-based functional assays for detection of residual or relapsed disease.

Example 2

Materials and Methods

A 74 y/o male who had been treated for CML with a BCR-ABL1-targeted tyrosine kinase inhibitor for eight years presented with early molecular relapse after stopping treatment. The complete blood count was: WBC of 7.9K/ul (PMN: 3.43, lymph: 3.41, mono: 0.82), and PLT: 177K/uL, and normal Hgb. BCR-ABL1 p210: 0.285 IS. The unmodified (baseline) whole blood sample obtained with informed consent was fixed in the BD Phosflow lyse/fix buffer 4 hours post-collection, washed with wash buffer, and stained with a panel of metal-conjugated antibodies. Surface staining was performed with antibodies against 1) marker of immaturity (CD34-173Yb), 2) lineage-determining antigens: CD4-145Nd, CD20-147Sm, CD15-148Nd, CD7-149Sm, CD3-150Nd, CD45-154Sm, CD19-156Gd, CD11c-159Tb, CD14-160Gd, CD16-166Er, CD24-168Er, CD8a-170Er, CD66-171Yb, CD56-175Lu, CD33-176Yb; 3) activation- and maturation-associated antigens: CD27-152Sm, CD45RA-153Eu, IgD-161Dy, CD38-167Er, HLA-DR-174Yb; and 4) cytokine receptors in proliferative signaling pathways: KIT/CD117-169Tm, IL3R/CD123-151Eu, IL7R/CD127-158Gd. The sample was permeabilized with 100% methanol–80° C. overnight, washed 2× in wash buffer, and labeled for analysis of select IC antigens using the following antibodies: p-p38 MAP kinase-157Gd, p-ERK 1/2-162Dy, p-STAT3-164Dy, p-S6 kinase-165Ho; p-STAT5A-172Yb; and total IKB☐-163Dy for 30 minutes at RT. After 1× wash, the sample was treated with DNA Iridium nucleic-acid intercalator for a final concentration of 1:2000. The data were captured on CyTOF and analyzed by traditional gating tools and high dimensional data analysis algorithms including Spanning Tree Progression of Density Normalized Events (SPADE).

Results

Figure 10:
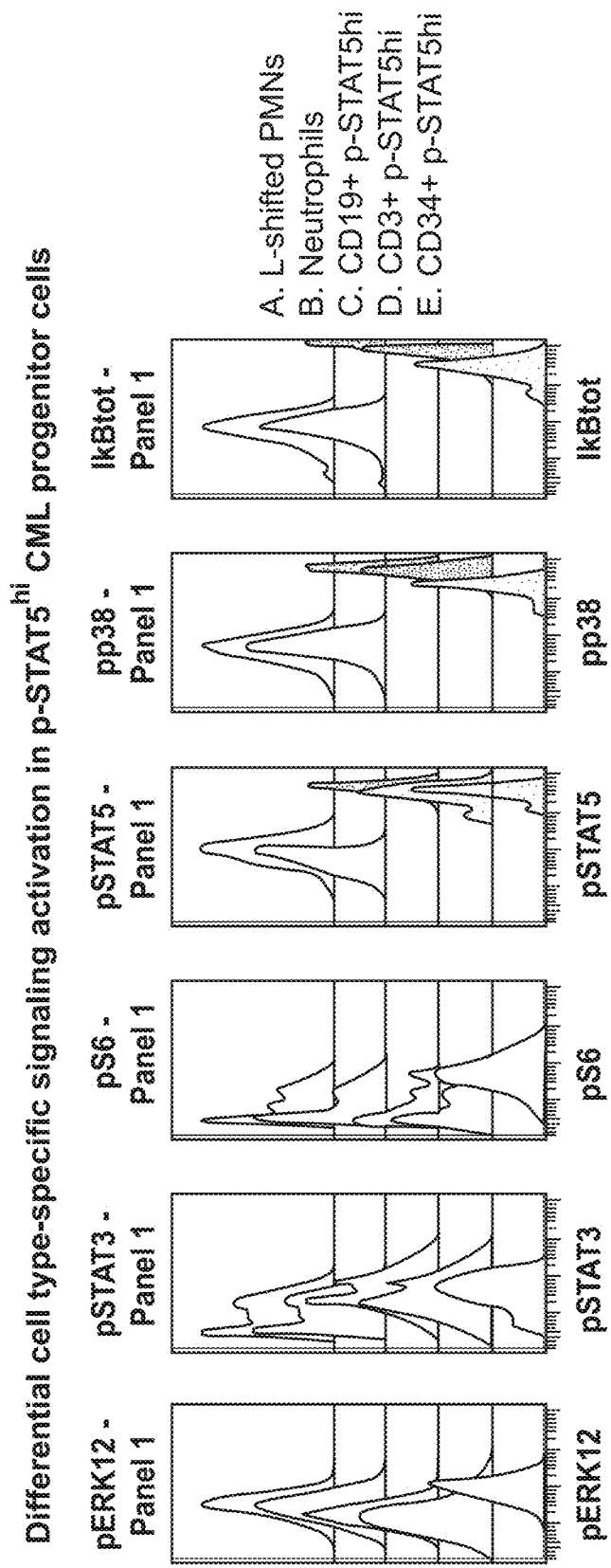
FIG. 10 shows differential cell type-signaling activation in p-STAT$^{hi}$ CML stem/progenitor cells. It illustrates differential STAT5 and p38 MAPK, and IKB kinase activities within the individual p-STAT5$^{hi}$ cell-types as compared to mature neutrophils and immature (L-shifted) neutrophils. Baseline p-STAT5 was low in mature neutrophils compared to L-shifted neutrophils suggesting loss of p-STAT5 as the myeloid lineage cells undergo final maturation and apoptosis. The p-STAT5$^{hi}$ myeloid progenitor/stem cells had lower p38 MAPK and IKB kinase compared to the p-STAT5$^{hi}$ lymphoid progenitor cells.
Figure 11:
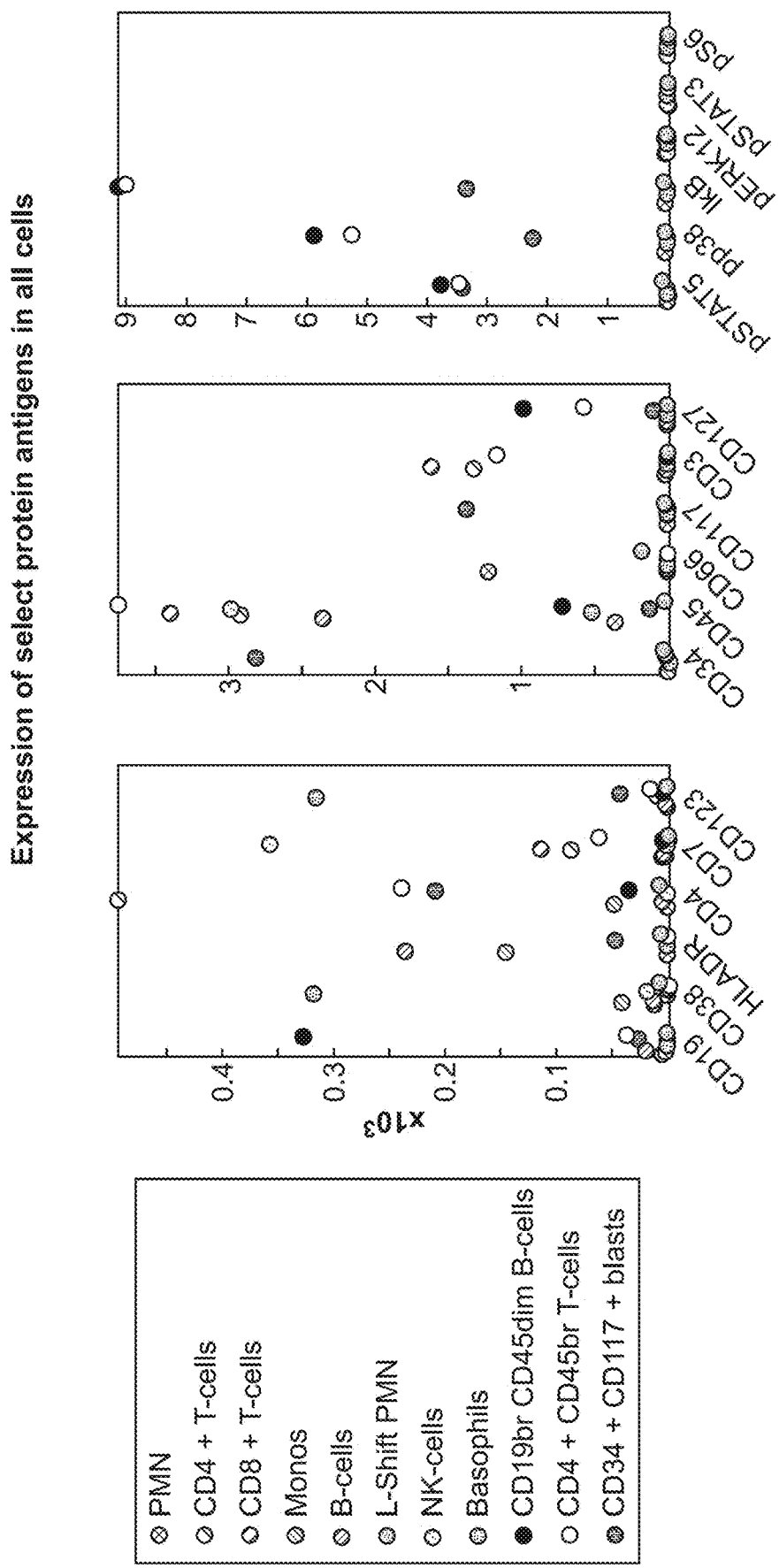
FIG. 11 shows a high dimensional data plot capturing select antigen expression profile in individual cell types displayed with relative cell frequencies. Cells with high IC activities included CD19+/CD45$^{lo}$/IL7R$^{hi}$ and CD3+/CD45+/IL-7R$^{lo}$ lymphoid progenitors and less frequent CD34+/CD117+/IL7R−/IL3R$^{lo}$ myeloid progenitor/stem cells.
Figure 12:
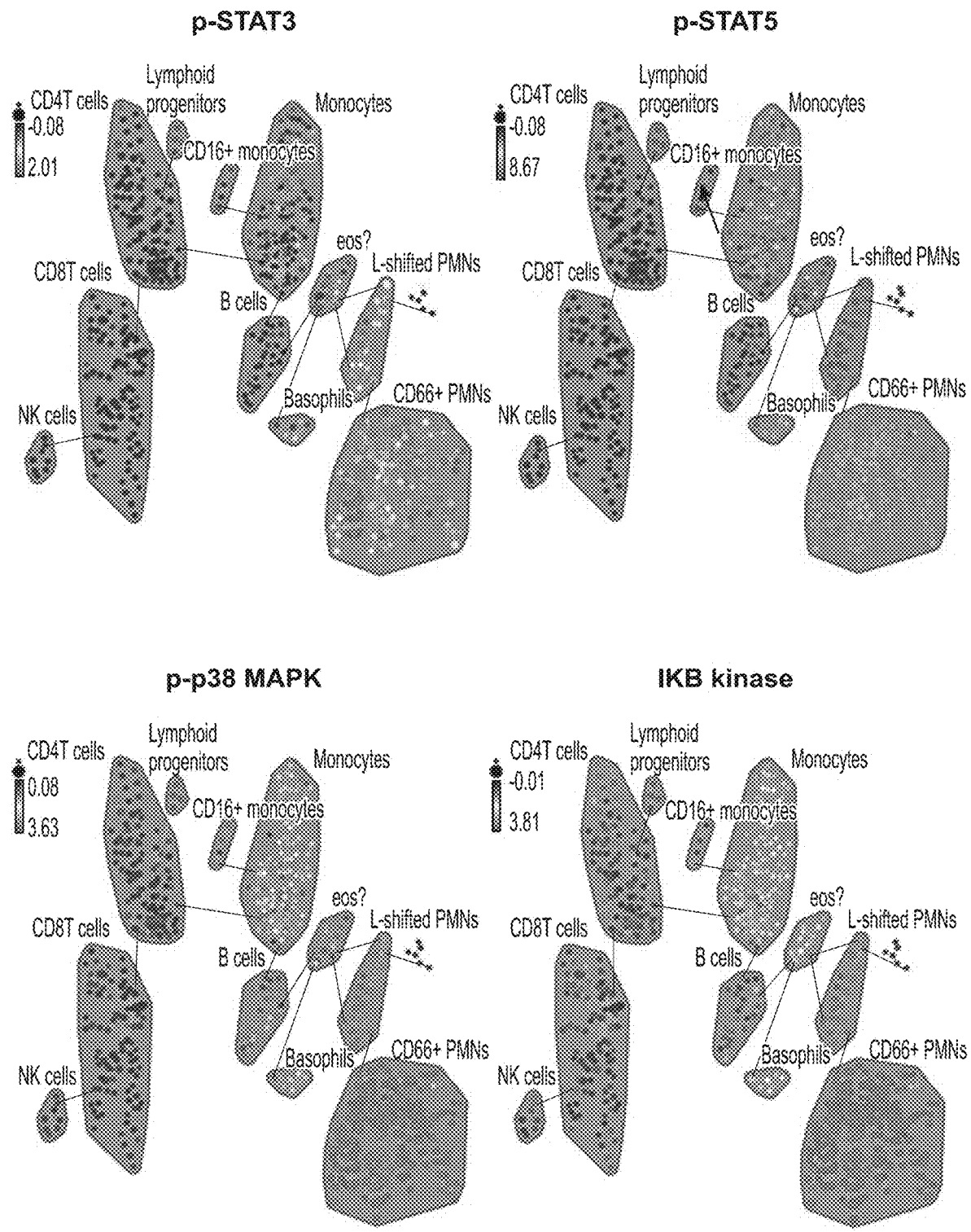
FIG. 12 illustrates mass cytometry data in high dimensional SPADE views to capture expression level of selected readouts in all cells of whole blood with relapsed CML. It illustrates high baseline p-STAT5 activity in lymphoid correlated with p-STAT3 and p-38 MAPK activities and total IKB levels.
Figure 13:
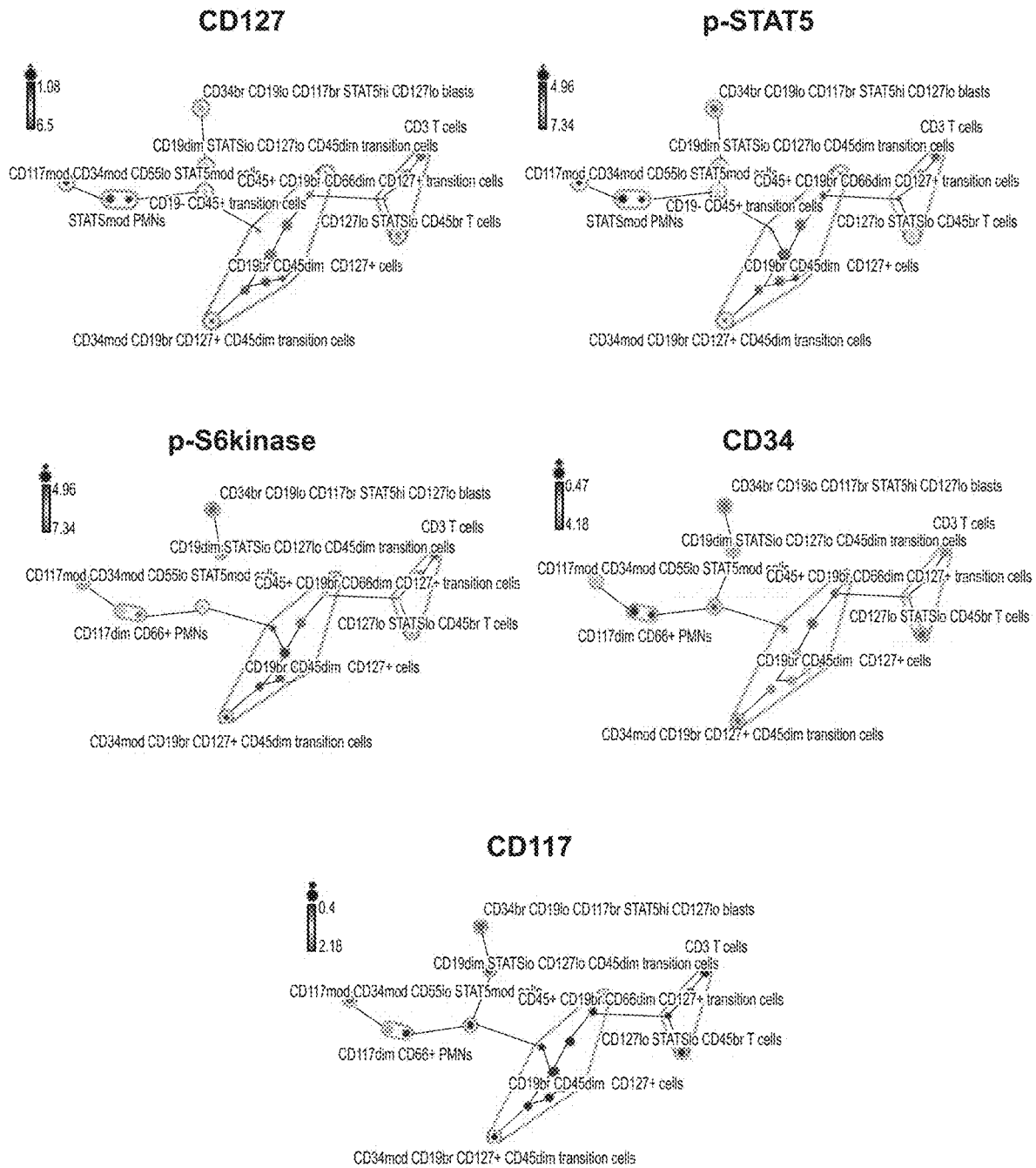
FIG. 13 SPADE analysis view of p-STAT5$^{hi}$ subpopulations shows the CD127$^{lo}$ stem/progenitor cells had relatively high pS6 kinase activity suggestive of mTOR activation.

In CML recurrence after stopping treatment in this case, the following observations were made:

By using CD45 and p-STAT5 bivariate plot, clusters of p-STAT$^{hi}$ cells were identified. Further bivariate gating revealed two minor lymphoid subpopulations—CD19+/CD20–/IgD–/CD66–/CD34$^{lo}$/CD45$^{lo}$ progenitor cells (0.36%) and CD3+/CD4+/CD45+T lymphocytes (0.24%)— with markedly high basal STAT5 and p38 activity that correlated with IL7R/CD127 expression such that IL7R– mature lymphocytes lacked high STAT5 or p38 MAPK activity levels (FIGS. 9-12). A minute myeloid blast population (p-STAT5$^{hi}$/IL3R+/IL7R$^{lo}$/CD34+/CD117+, 0.06%) was detected, with 2× lower p-38 MAPK activity and 3× lower IKB compared to the p-STAT5$^{hi}$/L-7R+ lymphoid progenitors (FIG. 10 and FIG. 13). The data suggest a role of IL-7R in receptor-mediated p-STAT5 and p-38 MAPK activation, with IL7R+/pSTAT5$^{hi}$/p38MAPK$^{hi}$ lymphoid cells and IL3R+/pSTAT5$^{hi}$/CD34+/CD117+ myeloid cells as potential cell-based biomarkers of relapsed CML and other myeloid neoplasms. Further, CD19+/IL7R+/pSTAT5$^{hi}$/p38MAPK$^{hi}$ lymphoid cells are likely BCR-ABL(+) and could be a potential cell-based biomarker for recurrent disease in BCR-ABL+ leukemias (which include CML and BCR-ABL1+ precursor B lymphoblastic leukemia). Additionally, the ratio of CD34+/p-STAT5$^{hi}$/p-p38MAPK$^{hi}$ cells compared to CD19+/p-STAT5$^{hi}$/p-p38MAPK$^{v.hi}$ and CD3+/p-STAT5$^{hi}$/p-p38MAPK$^{v.hi}$ cells identified with this approach could have prognostic relevance.

IL3R helps distinguish the myeloid stem/progenitor cells in myeloid neoplasms (myeloproliferative neoplasms, acute myeloid leukemia, myelodysplasia, myelodysplastic/myeloproliferative overlap syndromes) from normal physiologic stem/progenitor cells, and here elevated pS6 kinase activity suggests constitutive mTOR activation in IL3R+ cells (FIG. 13). In this case, the data provide evidence of relapsed leukemia based on cell type-specific functional activity. Thus, assays based on the above combination of markers are useful in detection of residual or early myeloid neoplasms.

The assay can be formulated for single tube high parameter analysis necessitating fewer cells than typical multiparameter FCM assays.

Data visualization algorithms help visualize modifications in select parameters and cell-types due to certain select perturbations, enabling high throughput data analysis and interpretation based on abnormal activation patterns.

Interpretation

Differential response to cytokine activation provided evidence for the role of pro-inflammatory milieu that favors myeloid maturation over lymphoid development in CML. The data provided support for the STAT5 pathway as a potential drug target in myeloid neoplasms including BCR/ABL-positive chronic myelogenous leukemia and BCR/ABL-negative chronic myeloproliferative neoplasms (such as primary myelofibrosis), acute myeloid leukemia; and Ph+B-lymphoblastic or biphenotypic leukemias. Cytokine responsiveness in stem/progenitor cells is a possible indicator of therapy responsiveness based on their known refractoriness to tyrosine kinase inhibitor and data supporting low cytokine responses.

Cytokine-induced effects on proliferative pathways can be indicative of response to targeted inhibitors. Given the crucial role of IL6, a gene regulated by BCL6 in CML pathogenesis, the data raised doubt on the efficacy of BCL6 repression.

Detection of rare cells with elevated STAT5 and p38 MAPK activity with possible signaling through IL-7R suggests importance of these survival pathways in CML.

Whether STAT5 activity correlates with BCR/ABL expression in all three cell types identified, and the potential prognostic and therapeutic relevance of rare circulating IL-7R/CD127+ cells expressing lymphoid markers in CML remains to be elucidated. The significance of the rare CD3+/CD45+/IL-7R+/p-STAT5$^{hi}$ T-cell subset as a possible immune escape mechanism or a survival mechanism maintaining chronicity is to be considered to be one possible mechanism but one that is not binding and the inventor does not which to be bound by any proposed mechanism. Thus, for minimal residual disease detection in a case of a hematopoietic stem cell neoplasm such as CML, T lymphoid progenitors with abnormal activity levels can be detected and are of potential prognostic relevance.

Example 3

This example, generally depicted in FIG. 14, demonstrates a prophetic panel of markers that contains a combination of surface and IC signaling markers, and additional optional panels of surface markers. The signaling biomarker signature could identify cell type(s) of interest based on analysis of fixed cells in one tube or assay. The surface marker profile and relative proportions of these cell types can be obtained through analysis of live cells in the additional other tubes or assay(s). Independent or integrated analysis of data acquired by each of the methods and extrapolation would be preferable to profile a particular cell subpopulation. For instance, the surface marker expression profile of a target cell subpopulation, initially identified by a certain set of IC attributes: [i1 (−), i2 (+++), i3 (−), i4 (++), i5 (+++)], can be derived by testing a limited set of antibodies measuring a small set of surface attributes on a fixed sample, and an extensive surface marker analysis on live cells. For example, the cells with the above IC marker profile could be found to have the following surface marker profile that then characterizes a particular cell type: [a(+, subset), b (++), c (−), d (−), e (++)], hence including those markers in the additional surface marker panels could derive the proportion and the extended profile of this cell type. Common factors that link the data from different tubes are light scatter properties Example 4

This example is generally depicted in FIG. 15. For myeloid stem cell neoplasms, such a 3-tube panel can measure the expression of following surface markers by labeling of live cells: CD3, CD4, CD8, CD14, CD19, CD38, CD45, CD117, CD123, CD127, HLA-DR. The following surface and IC markers would be assessed on fixed cells (with or without cytokine stimulation): CD3, CD16, CD19, CD20, CD33, CD34, CD45, CD123, CD127, p-STAT5, p-p38 MAPK, (+/−p-CRKL). Known correlations between receptor and IC signaling molecules are considered for panel design. Signaling activity profile can define subsets of major cell types.

This example establishes cell subpopulations of interest due to their prognostic relevance and representing therapy targets are identified in a robust manner. Such a combination of assays can identify subpopulations with activated signaling pathways activated. In CML, these are activated downstream of BCR-ABL kinase. The cell subpopulations identified by high dimensional analysis include leukemic stem/progenitor cells, lymphoid progenitor cells and proliferative myeloid cells, with distinction from non-neoplastic cells. Besides neoplastic cells being delineated based on high oncogenic activity, the assays are designed to distinguish benign and reactive cells devoid of abnormally high and/or constitutive signaling activities. The set-up relies on potential correlations of certain IC markers, such as p-STAT5 and p-p38 MAPK, with certain surface markers such as CD117 in CD34+ blasts and CD127 in lymphoid progenitors that express CD3 and/or CD19, to characterize a cell type. Cell subset profiling is achieved by evaluating expression intensity of each surface marker to generate a surface expression profile, and assaying specific functional attributes to further sub-classify cell types.

For the purpose of identifying the lineage of cells with activated pathways, Tube 3 contains a set of surface markers and IC phosphoproteins for testing on fixed cells. A limited set of surface markers in this tube is selected such that at least two surface markers are positive and one is negative, in order to facilitate partial lineage identification of cells with high signaling activity. The limited surface markers in this tube label some of the major cell types in the blood or bone marrow (B cells, T cells, monocytes, CD34+ blasts), whereas surface markers in the other panels allow identification of all identifiable cell subpopulations in the specimen. Using correlations between IC signaling molecules and surface receptors, an assay that performs only the surface markers can be designed. For example, Tube 4 is designed to a set of surface markers for targeted analysis of CD117+ myeloid and CD127+ lymphoid progenitors. The extended profile and relative proportions of "progenitor" cell types (as the index cell types of interest in this illustration) can be obtained through live cell analysis.

Example 5

This example is generally depicted in FIG. 16A, FIG. 16B, and FIG. 16C shows data analysis for the respective control and patient samples treated ex vivo supporting the design of panel in Example 6.

Example 6

This example is generally depicted in FIG. 17. In testing for peanut allergy, such a 2-assay panel would measure the following surface markers by labeling live cells: CD3, CD14, CD16, CD19, CD38, CD45, CD61, CD123, HLA-DR. The following surface and IC markers would be assessed on fixed cells: CD3, CD45, CD123, HLA-DR, p-ERK, p-p38 MAPK. The p38 MAPK and ERK activities on basophils (CD45+, CD123+, HLA-DR−) would be assessed. For the purpose of phenotyping basophils with activated pathways, Tube 1 contains a set of surface markers to distinguish basophils from the major cell components in whole blood, and assess CD63 expression on basophils as a potential biomarker for clinical assessment of allergy.

Although the foregoing invention has been described in some detail by way of illustration and examples for purposes of clarity of understanding, it will be apparent to those skilled in the art that certain changes and modifications may be practiced without departing from the spirit and scope of the invention, which is delineated in the appended claims. Therefore, the description should not be construed as limiting the scope of the invention.

All publications, patents, and patent applications cited herein are hereby incorporated by reference in their entireties for all purposes and to the same extent as if each individual publication, patent, or patent application were specifically and individually indicated to be so incorporated by reference.

REFERENCES

1. Shapiro, H M. The evolution of cytometers. Cytometry Part A 2004, 58A: 13-20.
2. Carey J L, McCoy J P, and Keren D F. Flow Cytometry in Clinical Diagnosis. Singapore: American Society of Clinical Pathology, 2007.
3. Reynaud D, Pietras E, Barry-Holson K, Mir A, Binnewies M, Jeanne M, Sala-Torra O, Radich J P, Passegue, E. IL-6 controls leukemic multipotent progenitor cell fate and contributes to chronic myelogeneous development. Cancer Cell 2011, 20(5): 661-73.
4. Cell fixation and use in phospho-proteome screening. U.S. Pat. No. 7,326,577, Feb. 5, 2008.
5. Far D F, Peyron J F, Imbert V, Rossi B. Immunofluorescent quantification of tyrosine phosphorylation of cellular proteins in whole cells by flow cytometry. Cytometry 1994, 15(4): 327-34.
6. Perfetto S P, Chattopadhyay P K, Roederer, M. Seventeen-color flow cytometry: unraveling the immune system. Nat. Rev. Immunol. 2004, 4(8):648-55.
7. Chattopadhyay P K, Gaylord B, Palmer A, et al. Brilliant violet fluorophores: a new class of ultrabright fluorescent compounds for immunofluorescence experiments. Cytometry Part A. 2012, 81A: 456-66.
8. Ornatsky O, Bandura D, Baranov V, Nitz M, Winnik M A, Tanner S. Highly multi parametric analysis by mass cytometry. J Immunol. Methods 2010, 361(1-2): 1-20.
9. Tordesillas et al. Mass cytometry profiling the response of basophils and the complete peripheral blood compartment to peanut. Journal of Allergy and Clinical Immunology. 2016

What is claimed is:

1. A composition comprising,
   a) a combination of specific binding members comprising a detectable label, comprising:
      i) at least one identified cell surface specific binding member that specifically binds with at least one cell surface antigen, and
      ii) at least one identified intracellular (IC) specific binding member that specifically binds with at least one IC antigen; and
   b) a physiological acceptable carrier;
   wherein said specific binding members can specifically bind with and identify one or more clinically relevant cell types in a biological sample comprising cells from a sample from a subject having or suspected of having allergy, peanut allergy, or autoimmune condition;
   wherein said composition of matter can label and identify cell populations relating to allergy, peanut allergy, or autoimmune condition;
   wherein said combination of specific binding members specifically bind with at least, p-p38MAPK and p-ERK as markers of activated basophils, or a combination thereof, and
   wherein said combination of specific binding members additionally bind with pp38 MAPK$^{hi}$ cells to distinguish cells based on expression of and presence or absence of or expression level of lineage-associated markers that comprise CD45 and CD123 and platelet adhesion and degranulation markers that comprise CD61 and CD63 to distinguish patient subgroups with p-p38MAPK+/CD63− or p-p38MAPK+/CD63+ basophils.

2. A method of predicting the cause of disease relapse, guiding disease therapy, and/or predicting disease outcome in a subject, comprising the steps:
   (a) labeling a first aliquot from a cell sample that contains a population of cells from the subject with surface antibodies only;
   (b) contacting a second aliquot from the cell sample with one or more reagents that fixes and permeabilizes the sample, thereby producing a fixed and permeabilized cell population;
   (c) contacting the fixed and permeabilized cell population with a combination of specific binding members that are directed to cellular biomarkers, wherein said specific binding members are directed at surface and IC biomarkers selected from the group consisting of CD3, CD4, CD8a, CD11c, CD14, CD16, CD19, CD33, CD34, CD38, CD45, CD56, CD66, KIT/CD117, IL3R/CD123, p-p38 MAPK, p-ERK 1/2, total IKB, p-STAT3, p-STAT5, and pS6 kinase; and
   (d) identifying one or more subsets of cells with abnormally high signaling activities as assessed by their binding to one of the binding members directed at p-STAT5, p-STAT3, p-p38 MAPK, p-ERK 1/2, or p-S6 kinase and administering therapeutics to said subject,
   wherein the resulting subset is indicative of disease relapse or recurrence in the subject;
   wherein said disease condition is selected from the group consisting of neoplastic states diagnosed as hematopoietic stem cell neoplasms, chronic myeloid leukemia, de novo acute myeloid leukemia, acute myeloid leukemia arising from a myelodysplastic syndrome or a myeloproliferative neoplasm, and lymphoma.

3. The method of claim 2, wherein said specific binding members are directed to surface receptor or receptor type proteins comprising KIT, IL3R, CD45; and IC functional proteins comprising p-STAT5, p-STAT3, p-p38 MAPK, p-ERK 1/2, and p-S6 kinase.

4. The method of claim 3, wherein said identifying one or more subsets within the cell population based on abnormally high expression of activated proteins based on phosphorylation of such proteins on one or more amino acids, wherein said activated proteins comprise p-STAT5, p-STAT3, p-p38 MAPK, p-ERK 1/2, and p-S6 kinase.

5. The method of claim 4, wherein said identifying one or more subsets of cells comprises single cell analysis by cytometry.

6. The method of claim 2, wherein each different specific binding member comprises a different metal tag or reporter molecule with panel configuration compatible with the instrument on which samples are analyzed.

7. The method of claim 2, wherein at least one modulating substance is contacted with the second aliquot for targeted stimulation or inhibition of certain cells prior to contacting the sample with one or more reagents that fixes and permeabilizes the sample.

8. The method of claim 7, wherein the at least one modulating substance comprises at least one cytokine or growth factor or inhibitor.

9. The method of claim 8, wherein the cytokine is selected from a group consisting of IL3, IL6, IL 7, IFNa2, EPO, and G-CSF.

10. The method of claim 2, wherein the sample that contains a population of cells comprises a cell line, fresh or frozen mononuclear cells, a fresh human sample, a fresh human sample in a preservative, or a tissue sample selected from blood, marrow, fine needle aspirate, and tissue biopsy sample.

11. The composition of claim 1, wherein the subject has or is suspected of having peanut allergy; and wherein said composition of matter can label and identify cell populations relating to peanut allergy.

* * * * *